(12) United States Patent
Chen

(10) Patent No.: US 11,200,443 B2
(45) Date of Patent: Dec. 14, 2021

(54) IMAGE PROCESSING APPARATUS, IMAGE PROCESSING METHOD, AND IMAGE PROCESSING SYSTEM

(71) Applicant: CANON KABUSHIKI KAISHA, Tokyo (JP)

(72) Inventor: Bin Chen, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 77 days.

(21) Appl. No.: 16/402,066

(22) Filed: May 2, 2019

(65) Prior Publication Data

US 2019/0258892 A1 Aug. 22, 2019

Related U.S. Application Data

(63) Continuation of application No. PCT/JP2017/035270, filed on Sep. 28, 2017.

(30) Foreign Application Priority Data

Nov. 9, 2016 (JP) .............................. JP2016-218864

(51) Int. Cl.
*G06K 9/46* (2006.01)
*G06T 7/187* (2017.01)
*G06T 7/50* (2017.01)
*G06T 7/11* (2017.01)
*G06T 7/00* (2017.01)
(Continued)

(52) U.S. Cl.
CPC .............. *G06K 9/4638* (2013.01); *A61B 6/03* (2013.01); *G06T 1/00* (2013.01); *G06T 5/30* (2013.01); *G06T 7/00* (2013.01); *G06T 7/0012* (2013.01); *G06T 7/11* (2017.01); *G06T 7/187* (2017.01); *G06T 7/50* (2017.01); *G06T 7/60* (2013.01); *G06K 2209/05* (2013.01); *G06T 2207/30064* (2013.01); *G06T 2207/30096* (2013.01)

(58) Field of Classification Search
CPC ... A61B 6/03; G06T 1/00; G06T 2207/10081; G06T 2207/30064; G06T 2207/30096; G06T 5/30; G06T 7/00; G06T 7/0012; G06T 7/11; G06T 7/187; G06T 7/50; G06T 7/60; G06T 7/62; G06K 2209/05; G06K 9/4638
See application file for complete search history.

(56) References Cited

U.S. PATENT DOCUMENTS 5,185,809 A * 2/1993 Kennedy ................ A61B 5/055
382/131
5,881,124 A * 3/1999 Giger .................... G06T 7/0012
250/363.04
(Continued)

FOREIGN PATENT DOCUMENTS

JP 2007-312892 A 12/2007
JP 2008-503294 A 2/2008
(Continued)

*Primary Examiner* — Ian L Lemieux
(74) *Attorney, Agent, or Firm* — Canon U.S.A., Inc. IP Division

(57) ABSTRACT

An image processing apparatus extracts a first region and a second region from a medical image, identifies a third region that is included in the second region and that is at a distance greater than or equal to a threshold from the first region, and acquires a feature value that is a value indicating a feature of the second region on the basis of the third region.

6 Claims, 14 Drawing Sheets

(51) Int. Cl.
  *G06T 1/00* (2006.01)
  *A61B 6/03* (2006.01)
  *G06T 7/60* (2017.01)
  *G06T 5/30* (2006.01)

(56) References Cited

U.S. PATENT DOCUMENTS

| | | | |
|---|---|---|---|
| 6,246,784 B1* | 6/2001 | Summers | G06K 9/00201 382/128 |
| 6,549,646 B1* | 4/2003 | Yeh | G06K 9/6814 382/132 |
| 9,449,247 B2* | 9/2016 | Yamada | G06T 7/12 |
| 2003/0099384 A1* | 5/2003 | Zeng | G06T 7/0012 382/128 |
| 2003/0099389 A1* | 5/2003 | Zeng | G06T 7/0012 382/131 |
| 2003/0099390 A1* | 5/2003 | Zeng | G06T 7/0012 382/131 |
| 2004/0064029 A1* | 4/2004 | Summers | G16H 15/00 600/407 |
| 2004/0086161 A1* | 5/2004 | Sivaramakrishna | G06T 7/0012 382/131 |
| 2005/0207630 A1* | 9/2005 | Chan | A61B 6/583 382/131 |
| 2005/0286750 A1 | 12/2005 | Dehmeshki | |
| 2007/0274583 A1* | 11/2007 | Sugiyama | G06T 11/008 382/131 |
| 2008/0137921 A1* | 6/2008 | Simon | G06T 7/11 382/128 |
| 2009/0129673 A1* | 5/2009 | Simon | G06T 7/11 382/173 |
| 2015/0254842 A1* | 9/2015 | Brown | G06T 7/187 382/131 |
| 2015/0348262 A1* | 12/2015 | Chen | G06T 7/11 382/131 |
| 2015/0356730 A1* | 12/2015 | Grove | G06T 7/64 382/124 |
| 2015/0379709 A1* | 12/2015 | Liang | G06T 7/40 382/131 |
| 2016/0260211 A1* | 9/2016 | Gillies | G16H 50/30 |
| 2017/0039737 A1* | 2/2017 | Madabhushi | A61B 5/08 |
| 2017/0140534 A1* | 5/2017 | Chen | G06T 7/0012 |
| 2017/0256062 A1* | 9/2017 | Furukawa | G06K 9/6224 |
| 2018/0025250 A1* | 1/2018 | Chen | G06K 9/46 382/292 |
| 2018/0181828 A1* | 6/2018 | Sakamoto | G06T 11/003 |
| 2019/0046127 A1* | 2/2019 | Furukawa | A61B 6/03 |
| 2019/0057503 A1* | 2/2019 | Nakamura | G06T 7/0012 |
| 2019/0156954 A1* | 5/2019 | Madabhushi | G16H 30/20 |
| 2019/0258892 A1* | 8/2019 | Chen | G06T 1/00 |
| 2020/0226746 A1* | 7/2020 | Schwartzbard | A61B 6/032 |
| 2021/0118130 A1* | 4/2021 | Zhang | G06T 11/00 |

FOREIGN PATENT DOCUMENTS

| | | |
|---|---|---|
| JP | 2011-135938 A | 7/2011 |
| WO | 2006000738 A1 | 1/2006 |

* cited by examiner

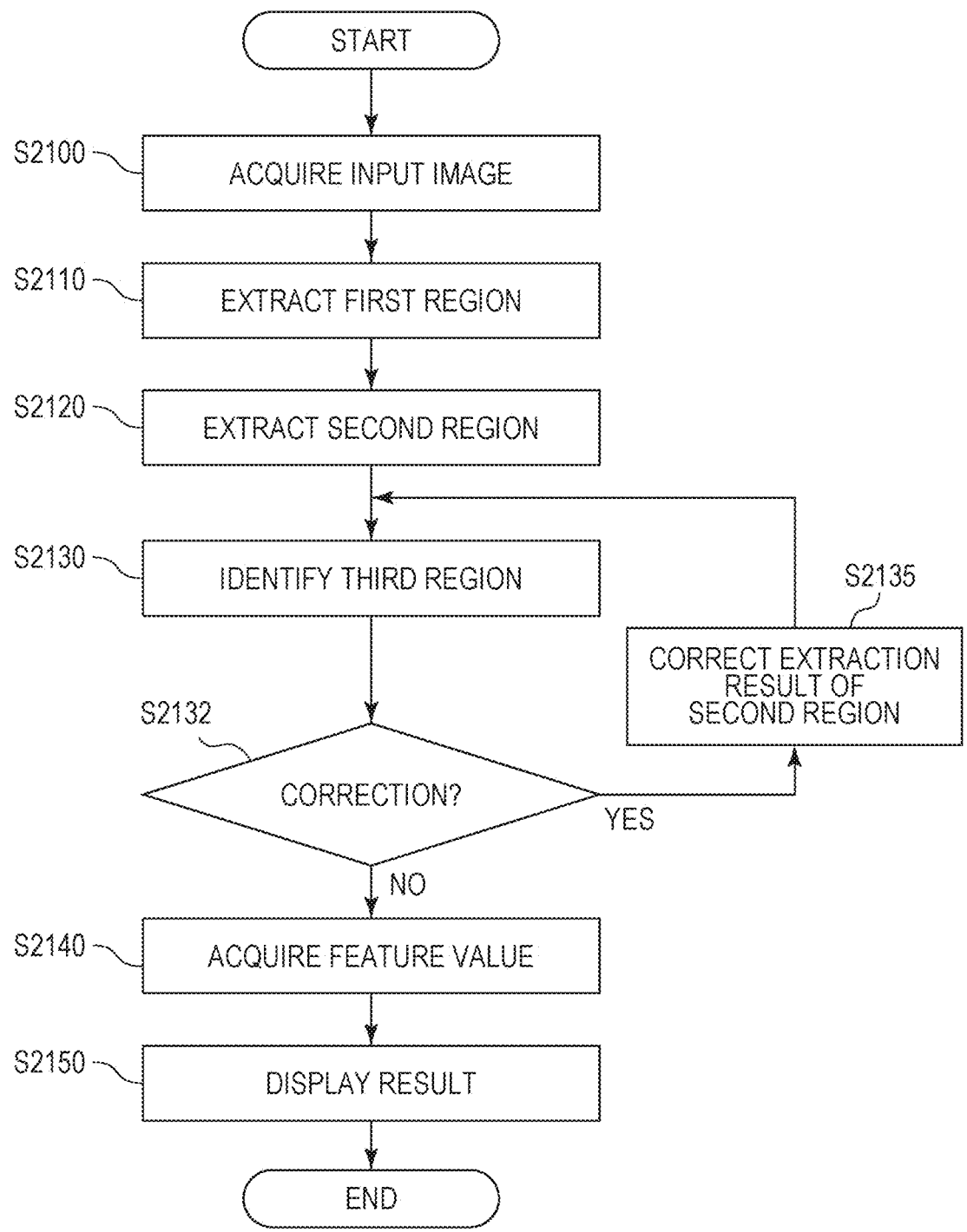

IMAGE PROCESSING APPARATUS, IMAGE PROCESSING METHOD, AND IMAGE PROCESSING SYSTEM

CROSS-REFERENCE TO RELATED APPLICATIONS

This application is a Continuation of International Patent Application No. PCT/JP2017/035270, filed Sep. 28, 2017, which claims the benefit of Japanese Patent Application No. 2016-218864, filed Nov. 9, 2016, both of which are hereby incorporated by reference herein in their entirety.

TECHNICAL FIELD

The present invention relates to an image processing apparatus, an image processing method, and an image processing system.

BACKGROUND ART

Recently, there has been growing interest in technology for computer aided diagnosis (CAD) using information obtained by analyzing medical images using computers to assist diagnosis. In such technology, to analyze features of lesions or judge the benignity or malignancy of the lesions, accuracy for identifying and extracting regions to be analyzed is important. Some regions to be analyzed are located near other structures such as organs, blood vessels, or lesions. PTL 1 discloses that when a region to be analyzed and any other region, which are joined to each other, are extracted as a single structure, the regions of the structure are reduced to separate the regions from each other.

CITATION LIST

Patent Literature

PTL 1 Japanese Patent Laid-Open No. 2007-312892

In some cases, a region to be analyzed may deform in shape when located near any other structure. Doctors may make diagnoses by observing regions less affected by the deformation. In CAD, regions less affected by the deformation may also be analyzed. Merely separating regions extracted as a single structure into a plurality of structures in accordance with a process for reducing the regions may be insufficient to make analysis taking into account that the structures are located near each other.

SUMMARY OF INVENTION

An image processing apparatus according to an embodiment of the present invention includes extraction means for extracting a first region and a second region different from the first region from a medical image, identification means for identifying a third region, the third region being included in the second region and being at a distance greater than or equal to a threshold from the first region, and acquisition means for acquiring a feature value on the basis of the third region, the feature value being a value indicating a feature of the second region.

Further features of the present invention will become apparent from the following description of exemplary embodiments with reference to the attached drawings.

BRIEF DESCRIPTION OF DRAWINGS

FIG. 12 is a flowchart illustrating an example process performed by the image processing apparatus according to the second embodiment.

DESCRIPTION OF EMBODIMENTS

Figure 1:
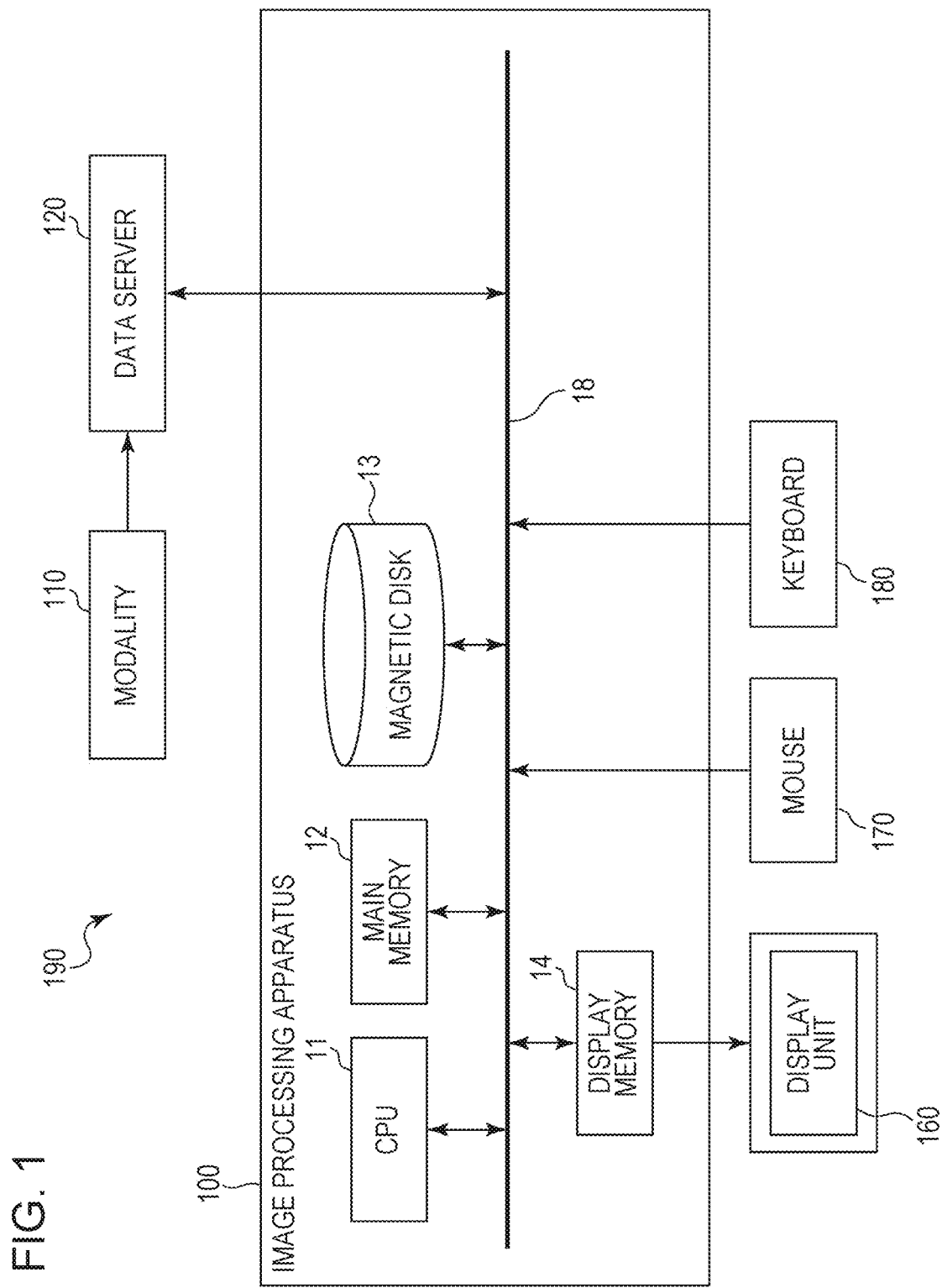
FIG. 1 illustrates an example hardware configuration of an image processing apparatus according to an embodiment of the present invention and an example configuration of a system including the image processing apparatus according to the embodiment of the present invention.

The following describes embodiments of the present invention with reference to the drawings.

First Embodiment

In recent years, an increasing number of medical images have been utilized for diagnosis and applications of the medical images to CAD have been expected to be available. For example, to analyze a suspected lesion region presented on a medical image for CAD, information on the shape or signal value (pixel value) of the suspected lesion region is used. For example, in the judgment of a pulmonary nodule that can be lung cancer, information on the shape of the pulmonary nodule is used as an index. A malignant pulmonary nodule is known to be likely to take a lobulated shape, and a benign pulmonary nodule is known to be likely to take a round shape.

However, lesions may occur near peripheral structures such as peripheral organs or other lesions. In this case, a lesion may greatly differ in shape depending on whether the lesion is attached to a peripheral structure (attached region) or not (unattached region). That is, a portion of a lesion, which is located near any other structure, may deform in shape. For example, the pleura may be indented towards a nearby pulmonary nodule, which causes a deformation such as a pleural invagination. In terms of features such as density in pixel value, the boundary between a lesion region and a nearby structure may be unclear.

When a doctor makes diagnosis while observing a medical image, the observation may be mainly focused on an unattached region, which is considered to be less affected by the positioning of a lesion near any other structure. Also in CAD, therefore, when the lesion to be analyzed is located near any other structure, it may be preferable to perform analysis taking the influence of the positioning of the lesion near any other structure into account. An image processing apparatus 100 according to a first embodiment is intended to identify an attached region where the region to be analyzed is likely to be attached to any other region and an unattached region where the region to be analyzed is considered not to be attached to any other region in CAD, and to acquire a feature value while taking into account that the region to be analyzed is located near any other region. Even when a pulmonary nodule is not attached to the pleura, the pleura may be indented towards the pulmonary nodule if the pulmonary nodule is located near the pleura. In the following, a region affected by a lesion located near a peripheral structure even though not necessarily in contact with the peripheral structure, such as a pleural indentation region, is referred to as an attached region. The image processing apparatus 100 appropriately acquires a feature value such as the shape of the region to be analyzed. Accordingly, more accurate CAD can be performed.

In the following, a computed tomography (CT) image of the chest of a subject is used as an example of a medical image to be used for CAD, and an example will be described in which a pulmonary nodule near the pleura is to be analyzed. The image processing apparatus 100 identifies a boundary region (attached region) where a pulmonary nodule (lesion region) near the pleura is in contact with the pleura from the CT image to be used for CAD on the basis of the distance between the pulmonary nodule and the pleura. Then, the image processing apparatus 100 acquires the feature value of the lesion region on the basis of an unattached region, which is different from the attached region.

Configuration of Image Processing Apparatus 100

FIG. 1 illustrates an example hardware configuration of the image processing apparatus 100 and an example configuration of a system 190 including the image processing apparatus 100.

The image processing apparatus 100 is, for example, a computer and performs processing according to an embodiment of the present invention. The image processing apparatus 100 includes a central processing unit (CPU) 11, a main memory 12, a magnetic disk 13, and a display memory 14. The internal components of the image processing apparatus 100 are connected to one another via a common bus 18.

The CPU 11 mainly controls the operation of each component. The main memory 12 stores a control program to be executed by the CPU 11 or provides a work area when the CPU 11 executes a program. Examples of the main memory 12 include a random access memory (RAM) and a read only memory (ROM). The magnetic disk 13 stores an operating system (OS), device drivers for peripherals, and programs for implementing various software applications including a program for performing a process and the like described below. Examples of the magnetic disk 13 include a hard disk drive (HDD) and a solid state drive (SSD). The CPU 11 executes a program stored in the main memory 12 or the magnetic disk 13 to implement functions (software) of the image processing apparatus 100 illustrated in FIG. 1 and implement processes illustrated in flowcharts described below. The display memory 14 temporarily stores display data to be displayed on a display unit 160, for example.

Examples of the display unit 160 include a cathode-ray tube (CRT) monitor and a liquid crystal monitor. The display unit 160 displays an image, text, and so on based on data from the display memory 14. A mouse 170 and a keyboard 180 are operated by a user for pointing input and for character input or the like, respectively. The display unit 160 may be a touch panel monitor that accepts operation input. In this case, the mouse 170 and the keyboard 180 may be integrated into a function of the touch panel monitor. Alternatively, the image processing apparatus 100 may be connected to any other operation unit, such as a stylus pen, together with the touch panel monitor. In the following, a component configured to input information to the image processing apparatus 100, such as the mouse 170 or the keyboard 180, is referred to sometimes as an operation unit.

The CPU 11 is an example of a processor. The image processing apparatus 100 may include a plurality of processors. The image processing apparatus 100 may include a graphics processing unit (GPU) dedicated to image processing. The image processing apparatus 100 may include a field-programmable gate array (FPGA) for programming some or all of the processes described below, or include an application specific integrated circuit (ASIC) for a specific process. The main memory 12, the magnetic disk 13, and the display memory 14 are examples of a memory, and the image processing apparatus 100 may include a plurality of memories.

The system 190 includes the image processing apparatus 100 and a data server 120. In the first embodiment, the data server 120 is connected to a modality 110.

The modality 110 is a device for acquiring a medical image. Examples of the modality 110 include a CT device, a nuclear magnetic resonance imaging (MRI) device, and a digital radiography (DR) device for capturing a two-dimensional radiographic image. The modality 110 transmits an acquired medical image to the data server 120. A control unit (not illustrated) that controls the modality 110 may be included in the image processing apparatus 100.

The data server 120 is a device that stores medical images. Examples of the data server 120 include a picture archiving and communication system (PACS). The image processing apparatus 100 acquires a medical image from the data server 120 via a network such as a local area network (LAN).

Figure 2:
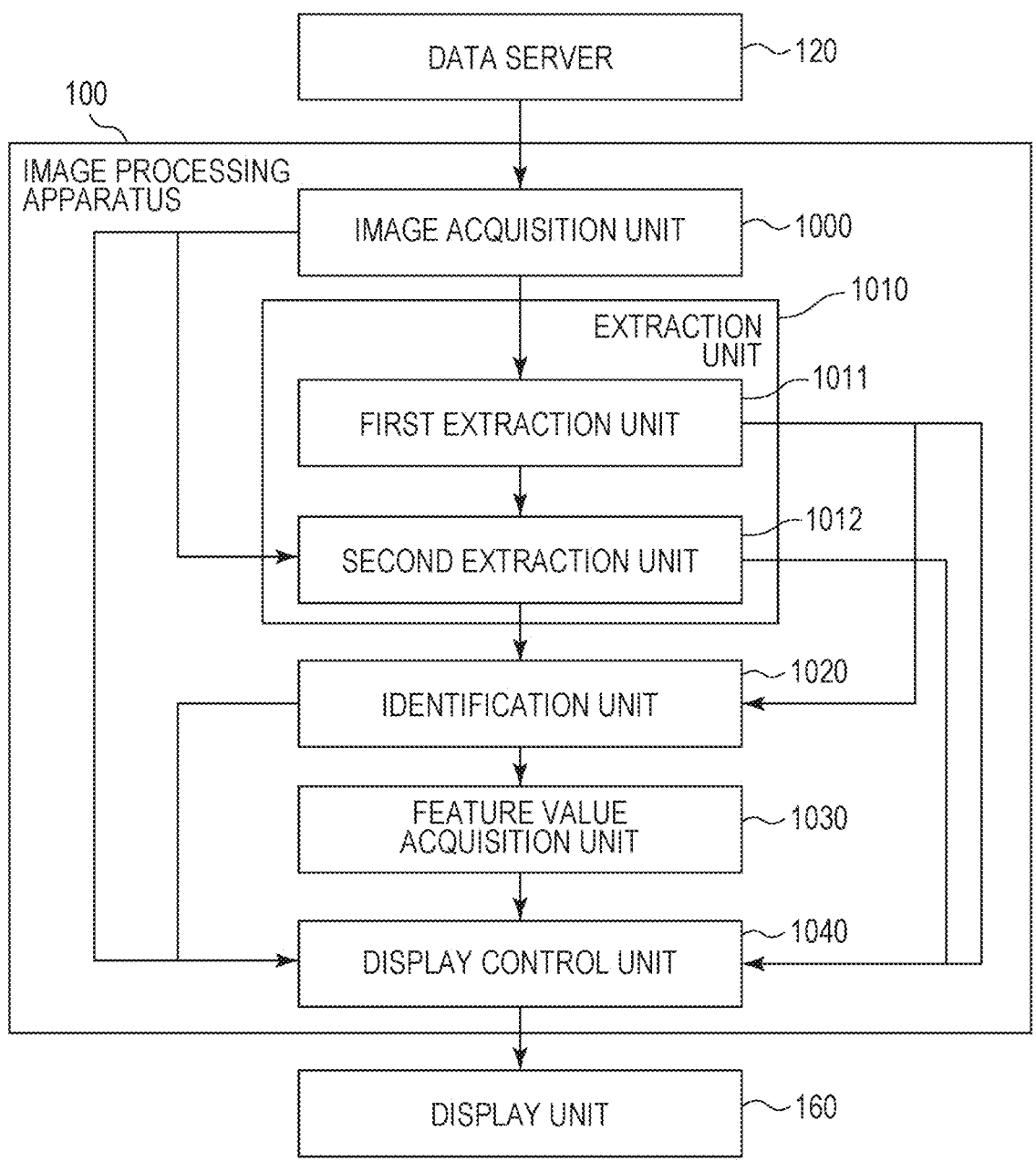
FIG. 2 illustrates an example functional configuration of an image processing apparatus according to a first embodiment.

FIG. 2 illustrates an example functional configuration of the image processing apparatus 100. The image processing apparatus 100 includes an image acquisition unit 1000, an extraction unit 1010, an identification unit 1020, a feature value acquisition unit 1030, and a display control unit 1040.

The image acquisition unit 1000 acquires a medical image from the data server 120. The image acquisition unit 1000 may acquire a medical image designated by a user or acquire a medical image under a predetermined condition. The image acquisition unit 1000 outputs an input image to the extraction unit 1010 and the display control unit 1040.

The extraction unit 1010 extracts a specific region from the medical image (hereinafter referred to as the input image) acquired by the image acquisition unit 1000 for analysis in CAD. In the first embodiment, the extraction unit 1010 includes a first extraction unit 1011 and a second extraction unit 1012.

The first extraction unit 1011 extracts a region of the anatomical structure of the subject from the input image. In the example of the chest CT image, the first extraction unit 1011 extracts a region of structures such as lung fields, the pleura, bronchi, and blood vessels. The region extracted by the first extraction unit 1011 is hereinafter referred to sometimes as a first region. A region of the anatomical structure is an example of the first region. The first extraction unit 1011 outputs information on the extracted region to the second extraction unit 1012, the identification unit 1020, and the display control unit 1040.

The second extraction unit 1012 extracts a lesion region to be analyzed from the input image. In the example of the chest CT image, the second extraction unit 1012 extracts a pulmonary nodule region. When a plurality of lesion regions are extracted, the second extraction unit 1012 may select one lesion region of interest. The following describes an example in which a single lesion region of interest is extracted by the second extraction unit 1012. The region extracted by the second extraction unit 1012 is hereinafter referred sometimes as a second region. A lesion region is an example of the second region. The second extraction unit 1012 outputs information on the extracted region to the identification unit 1020 and the display control unit 1040.

The identification unit 1020 identifies a region where the lesion region is located near any other structure, that is, an attached region, on the basis of the processing results obtained by the first extraction unit 1011 and the second extraction unit 1012. In the first embodiment, the identification unit 1020 identifies an attached region within the pulmonary nodule region extracted by the second extraction unit 1012 on the basis of the distance from a pleural region extracted by the first extraction unit 1011. That is, the identification unit 1020 identifies a sub-region that is included in the lesion region as an attached region. In the following, the attached region identified by the identification unit 1020 is referred to sometimes as a fourth region. Further, the identification unit 1020 identifies a region different from the attached region as an unattached region. In the first embodiment, the identification unit 1020 identifies a region included in the lesion region and not including the attached region as an unattached region. The unattached region is not limited to that in the example described above and may be any region that is different from the attached region and that is less affected by the positioning of the lesion region near any other region during analysis. In the following, the unattached region identified by the identification unit 1020 is referred to sometimes as a third region. The identification unit 1020 outputs information on the identified regions to the feature value acquisition unit 1030 and the display control unit 1040.

The feature value acquisition unit 1030 acquires a feature value, which is a value indicating a feature of the lesion region extracted by the second extraction unit 1012. The acquired feature value may be represented as a value such as the mean or variance of density (luminance) of the region to be analyzed in the input image or a value based on filter output. The feature value may be represented as words representing a feature of the lesion region, or so-called findings, or may be represented as words converted based on the value described above. The feature value acquisition unit 1030 designates the lesion region extracted by the second extraction unit 1012 and the attached region and unattached region identified by the identification unit 1020 as analytical targets, and acquires a feature value. To acquire a feature value for the shape of the lesion region, such as circularity, among feature values, it is desirable to designate the unattached region identified by the identification unit 1020 as the analytical target. The feature value acquisition unit 1030 outputs information on the acquired feature value to the display control unit 1040. The following describes an example of acquiring a feature value for the shape of the lesion region by using the unattached region as the analytical target.

The display control unit 1040 controls the output of display data to be displayed on the display unit 160. In the first embodiment, the display control unit 1040 outputs display data for displaying on the display unit 160 pieces of information, namely, the input image acquired by the image acquisition unit 1000, information indicating the region extracted by the extraction unit 1010, the information identified by the identification unit 1020, and the information acquired by the feature value acquisition unit 1030, as appropriate, to the display unit 160.

The functional components of the image processing apparatus 100, described with reference to FIG. 2, may be distributed to a plurality of devices and implemented. The image processing apparatus 100 may be a workstation. The functions of each unit of the image processing apparatus 100 may be implemented as software operating on a computer, and software implementing the functions of each unit may operate on a server via a network such as a cloud network. In the following, it is assumed that the functional components are implemented by software operating on a locally installed computer.

Regarding Series of Processes

Figure 3:
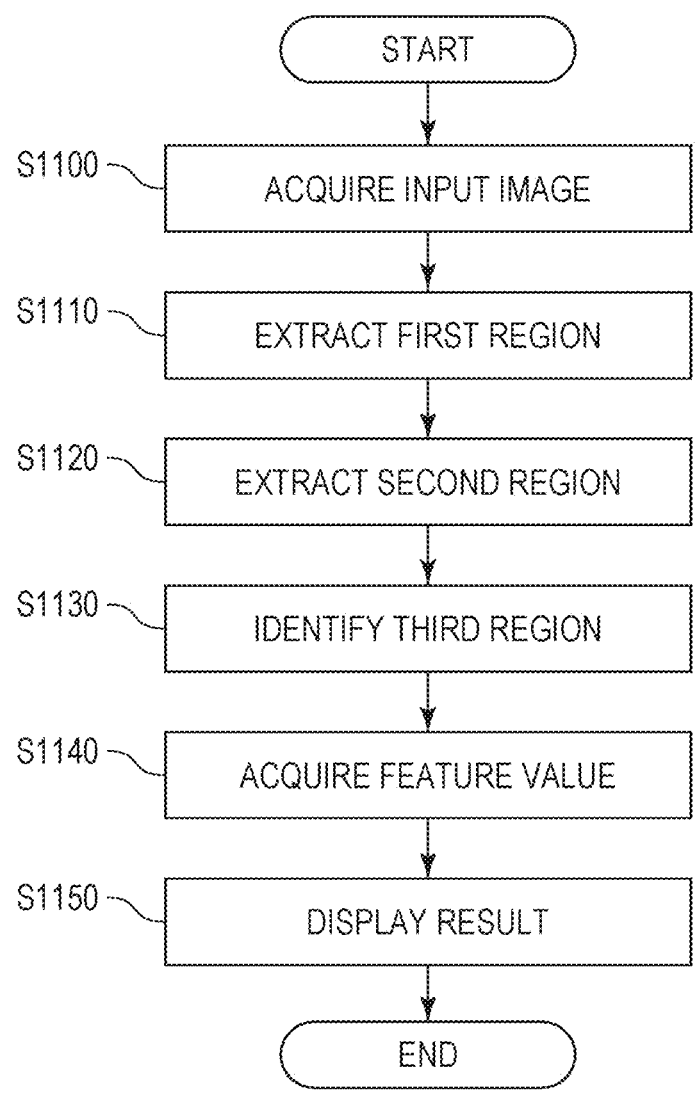
FIG. 3 is a flowchart illustrating an example process performed by the image processing apparatus according to the first embodiment.

FIG. 3 is a flowchart illustrating an example process performed by the image processing apparatus 100. In the following process, the processing operations are implemented by a processor such as the CPU 11 and are implemented by the processor executing a program stored in a memory such as the main memory 12, unless otherwise stated. Further, information processed by the processor is at least temporarily stored in the memory.

In step S1100, the image acquisition unit 1000 acquires an input image from the data server 120. In another example, the image acquisition unit 1000 directly acquires image data captured by the modality 110 via a communication means and acquires a medical image subjected to image processing or the like to obtain an image suitable for diagnosis as an input image according to this embodiment. For example, when the modality 110 is a CT device, a CT image having a pixel value based on a signal value, called a Hounsfield unit (HU) value, is acquired from the modality 110 as an input image.

The input image is constituted by a plurality of pixels whose positions can be each identified using three-dimensional Cartesian coordinates (x, y, z). The pixel size, which is one of the image attributes, is defined for each of three axis coordinate directions. The first embodiment describes an example in which the pixel sizes in the x, y, z directions are represented as r_size_x, r_size_y, and r_size_z, respectively, and all the values are 1.0 mm. The pixel values of pixels constituting the input image are defined for each value of three-dimensional coordinates (x, y, z). Accordingly, the input image can be regarded as data defined by a function $I(x, y, z)$ that uses three-dimensional coordinate values as an argument.

In step S1110, the first extraction unit 1011 extracts a first region from an input image $I(x, y, z)$. The first region is, for example, a region of the anatomical structure, such as lung fields on a chest CT image and the pleura adjacent to the lung fields. The first extraction unit 1011 extracts a lung field region, which is a region of the anatomical structure of the subject, from the input image $I(x, y, z)$. The lung field region includes regions such as an air (alveolar) region, some of the bronchi, some pulmonary vessels, and pulmonary nodules.

The first extraction unit 1011 performs a process, such as a threshold process, a process using a filter that enhances a specific shape, a process using the graph-cut method, a process using the level-set method, or a process using the organ atlas (model) based on anatomy, on the input image $I(x, y, z)$ to extract a region of the anatomical structure. Here, a technique using the graph-cut method will be described briefly, by way of example.

In the graph-cut method, first, a graph for the input image $I(x, y, z)$ is generated. The graph is constituted by nodes (image nodes), each of which corresponds to one of the pixels of the input image, a node representing a lung field region (terminal node F), a node representing a non-lung-field region (terminal node B), edges (n-link) each connecting adjacent image nodes, and edges (t-link) each connecting one of the image nodes and the two terminal nodes. Then, values each representing similarity of image density values (e.g., the reciprocal of the difference between the image density values) are calculated for all combinations of adjacent pixels. Then, the calculated values are each assigned to the edge (n-link) connecting the image nodes corresponding to the associated adjacent pixels as a weight. Further, for each pixel, a value representing a similarity between the pixel value of the pixel and the pixel value of a typical pixel in the lung field region (e.g., the reciprocal of the difference between image density values) is calculated. Then, the calculated value is assigned to the edge (t-link) connecting the image node corresponding to the pixel and the terminal node F as a weight. Likewise, for each pixel, a value representing a similarity between the pixel value of the pixel and the pixel value of a typical pixel in the non-lung-field region (e.g., the difference between image density values) is calculated and assigned to the edge (t-link) connecting the image node corresponding to the pixel and the terminal node B as a weight.

After the generation of a graph, the graph is divided into two subgraphs by using a graph segmentation algorithm (e.g., the Ford-Fulkerson algorithm). The graph is divided such that one of the subgraphs includes at least the terminal node F, and the other subgraph includes the terminal node B. As a result of the segmentation of the graph under the constraints described above, the graph is divided into two subgraphs by an edge (n-link) created between an image node corresponding to a "pixel likely to belong to the lung field region" and an image node corresponding to a "pixel likely to belong to the non-lung-field region". In this case, the subgraph (subgraph $G_F$) including the terminal node F includes the image node corresponding to the "pixel likely to belong to the lung field region". The subgraph (subgraph $G_B$) including the terminal node B includes the image node corresponding to the "pixel likely to belong to the non-lung-field region". The pixel nodes included in the subgraph $G_F$ are referred to as pixels belonging to the lung field region. The pixels corresponding to the pixel nodes included in the subgraph $G_B$ are referred to as pixels belonging to the non-lung-field region. In this way, an anatomical structure region (a lung field region) $V_{lung}$ is acquired.

In the graph creation process described above, if a pixel that certainly belongs to the lung field region is known in advance, the weight of the edge (t-link) created between the image node corresponding to the pixel and the terminal node F may be set infinite. Likewise, if a pixel that certainly belongs to the non-lung-field region is known in advance, the weight of the edge (t-link) created between the image node corresponding to the pixel and the terminal node B may be set infinite.

When an anatomical structure region (a lung field region) is extracted by using the techniques described above, the extraction of some regions, such as some of the bronchi, some pulmonary vessels, or pulmonary nodules, may fail. To address this, after the extraction of an anatomical structure region (a lung field region), a process for integrating the missing element regions into the anatomical structure region is performed. For example, the anatomical structure region (the lung field region) may be subjected to closing, which is one of the morphological operations. Through this process, regions such as some of the bronchi, some pulmonary vessels, and pulmonary nodules, which are present in the anatomical structure region (the lung field region), are included in the anatomical structure region (the lung field region).

The first extraction unit 1011 may extract, as a first region, an area designated by the user on an input image displayed on the display unit 160 by using the mouse 170 or the like. In the following, an extracted lung field region is represented as a lung field region $V_{lung}$.

The first extraction unit 1011 further extracts a pleural region. In the first embodiment, the first extraction unit 1011 extracts a pleural region after the acquisition of the lung field region $V_{lung}$. In the following, the extracted pleural region is represented as a pleural region $V_{pleural}$.

Figure 4:
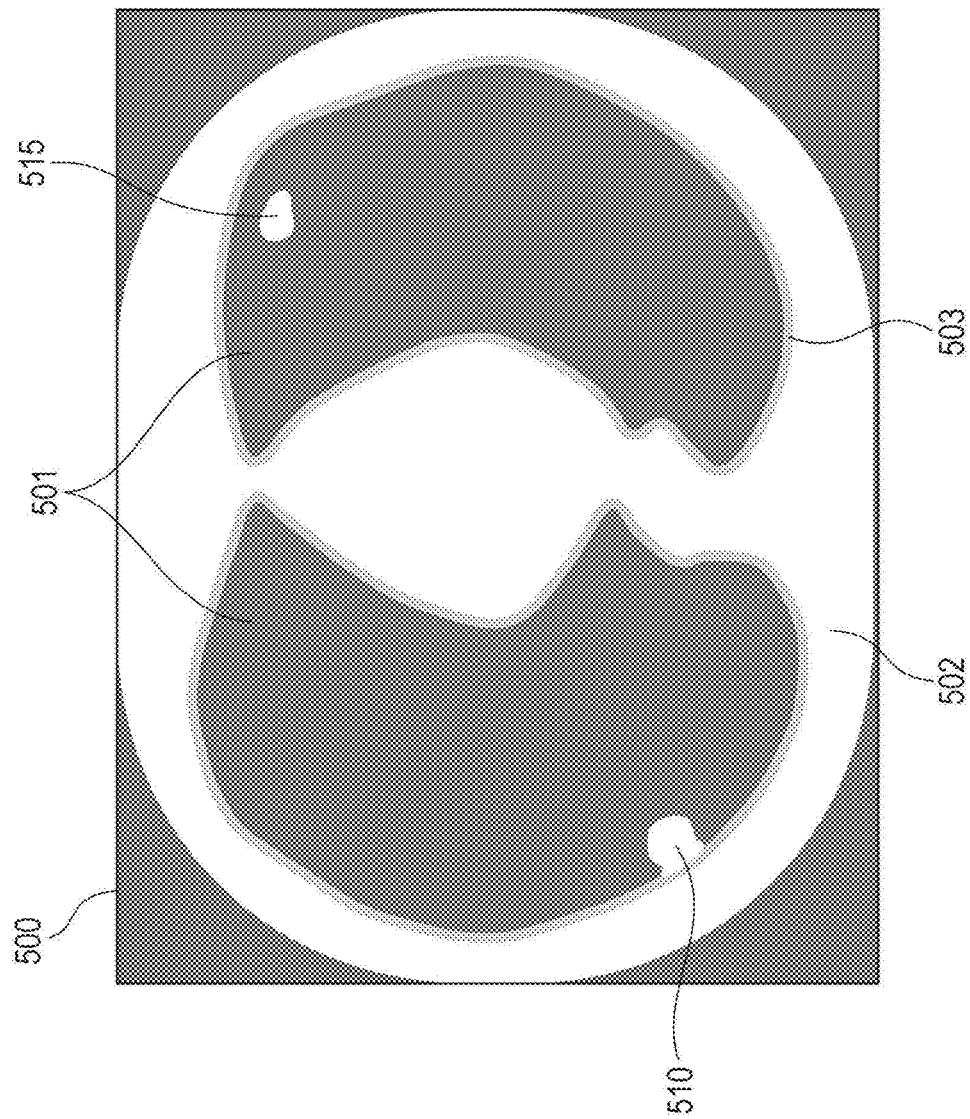
FIG. 4 illustrates an example of a medical image to be processed by the image processing apparatus according to the embodiment of the present invention.

FIG. 4 illustrates the anatomical structure of the chest including lung fields and pleura. On a CT image 500, the structure of the chest of the subject is presented. A chest wall region 502 outside lung field regions 501 is a region of the chest wall including the structure such as muscle, bone, lymphatic vessels, blood vessels, nerves, and fascia. In the example illustrated in FIG. 4, pulmonary nodules 510 and 515 are present in the lung field regions 501. Pleural regions 503 are located between the lung field regions 501 and the chest wall region 502. The pleura is constituted by a double-layered serosa that covers the lungs and the chest wall. The pleural regions 503 are thin membrane regions adjacent to the lung field regions 501 and the chest wall region 502.

The first extraction unit 1011 acquires, as the pleural region $V_{pleural}$, for example, a region that is located outside the lung field region $V_{lung}$ and that is at a distance less than or equal to a predetermined distance from the edge of the lung field region $V_{lung}$. In another example, the first extraction unit 1011 may enlarge the lung field region $V_{lung}$ with a predetermined magnification and acquire, as the pleural region $V_{pleural}$, a region corresponding to the difference between the enlarged lung field region and the original lung field region before enlargement.

The first extraction unit 1011 may further extract regions of other anatomical structures presented on the chest CT image, such as a pulmonary vessel region and a bronchus region, in addition to the lung field region $V_{lung}$ and the pleural region $V_{pleural}$. The first extraction unit 1011 may extract a region of an anatomical structure in accordance with CAD analysis or extract regions of all extractable structures among the anatomical structures presented on the input image I(x, y, z).

In step S1120, the second extraction unit 1012 extracts a second region from the input image I(x, y, z). The second region is a lesion region, for example, a pulmonary nodule.

The second extraction unit 1012 extracts a region of a lesion on the basis of information such as a characteristic signal value (pixel value) or shape of the target lesion. Specifically, the second extraction unit 1012 performs a process, such as a threshold process, a process using a filter that enhances a specific shape, a process using the graph-cut method, a process using the level-set method, or a process using the organ atlas (model) based on anatomy, on the input image I(x, y, z) to extract a region of the anatomical structure. The following describes the extraction of a pulmonary nodule region, by way of example.

The second extraction unit 1012 extracts a pulmonary nodule region from the lung field region $V_{lung}$ extracted in step S1110. First, the second extraction unit 1012 performs a threshold process or a process using a filter, such as a Hessian matrix, on the input image I(x, y, z) to detect a pulmonary nodule region from the lung field region $V_{lung}$. Then, the second extraction unit 1012 performs a process using the graph-cut method or a process using the level-set method on the detected pulmonary nodule region to extract the pulmonary nodule region.

Further, the second extraction unit 1012 may prompt the user to designate a target pulmonary nodule. In this case, the user designates coordinates belonging to the target pulmonary nodule by using the mouse 170 while referring to the input image displayed on the display unit 160. The second extraction unit 1012 acquires the designated coordinates as the coordinates of a seed point of the pulmonary nodule. The second extraction unit 1012 extracts the pulmonary nodule region by using information on the seed point in addition to the technique described above. Accordingly, the second extraction unit 1012 extracts a pulmonary nodule region including the coordinates designated by the user. As another example, the second extraction unit 1012 may perform a process on a volume of interest (VOI) image including a target pulmonary nodule region to extract the pulmonary nodule region.

In the following, a pulmonary nodule of interest to be analyzed is referred to as $C_{nodule}$. In the following, furthermore, the pulmonary nodule region extracted by the second extraction unit 1012 in step S1120 is referred to as a pulmonary nodule region $V_{nodule}$.

Pulmonary nodules may occur at various sites in the lungs. In the first embodiment, an example process will be described for acquiring a feature value, taking into account the influence of the attachment of the pulmonary nodule extracted in step S1120 to other structures.

In step S1130, the identification unit 1020 identifies a fourth region. The fourth region is an attached region that is included in the second region acquired in step S1120 and that is likely to be attached to other regions.

Figure 5A:
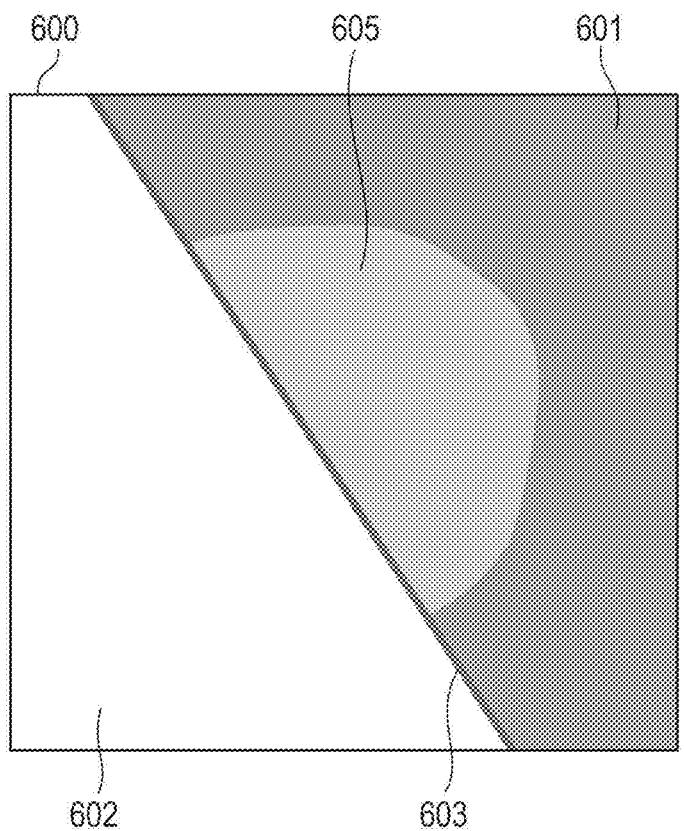
FIG. 5A illustrates a process performed by the image processing apparatus according to the embodiment of the present invention.
Figure 5B:
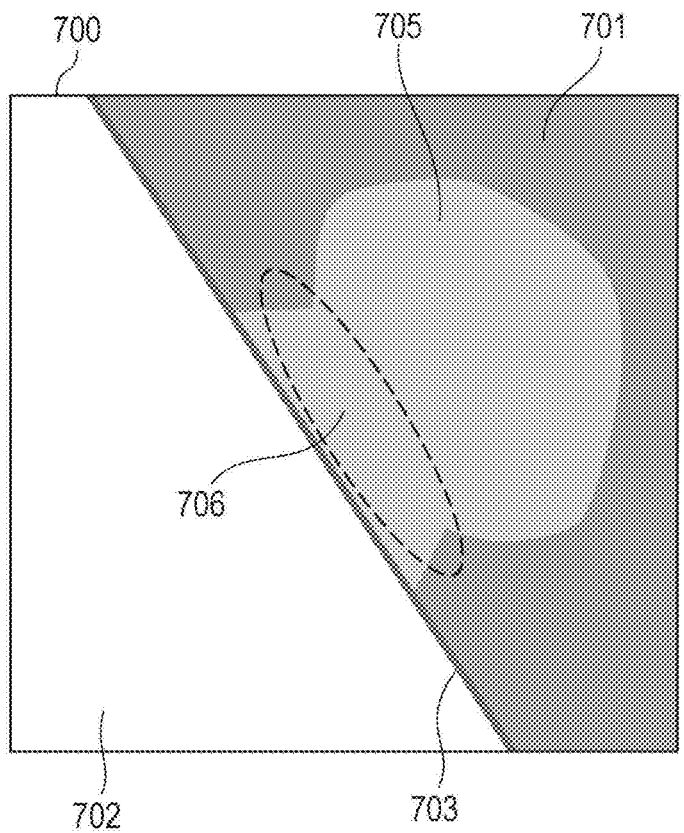
FIG. 5B illustrates a process performed by the image processing apparatus according to the embodiment of the present invention.

FIGS. 5A and 5B illustrate examples of a state in which a pulmonary nodule is attached to any other structure. In the following, a pulmonary nodule attached to any other structure is referred to sometimes as an attached pulmonary nodule.

Referring to FIG. 5A, a VOI image 600 includes a pulmonary nodule 605, which is an attached pulmonary nodule. The pulmonary nodule 605 is attached to a pleural region 603. Referring to FIG. 5B, a VOI image 700 includes a pulmonary nodule 705, which is an attached pulmonary nodule. The pulmonary nodule 705 is attached to a pleural region 703. In particular, in FIG. 5B, a pleural indentation region 706, where the pleura is indented towards a pulmonary nodule, is observed in a region where the pulmonary nodule 705 and the pleural region 703 are attached to each other. When a pleural indentation is observed, a clear boundary may be difficult to define between the pleura and the pulmonary nodule.

Figure 6A:
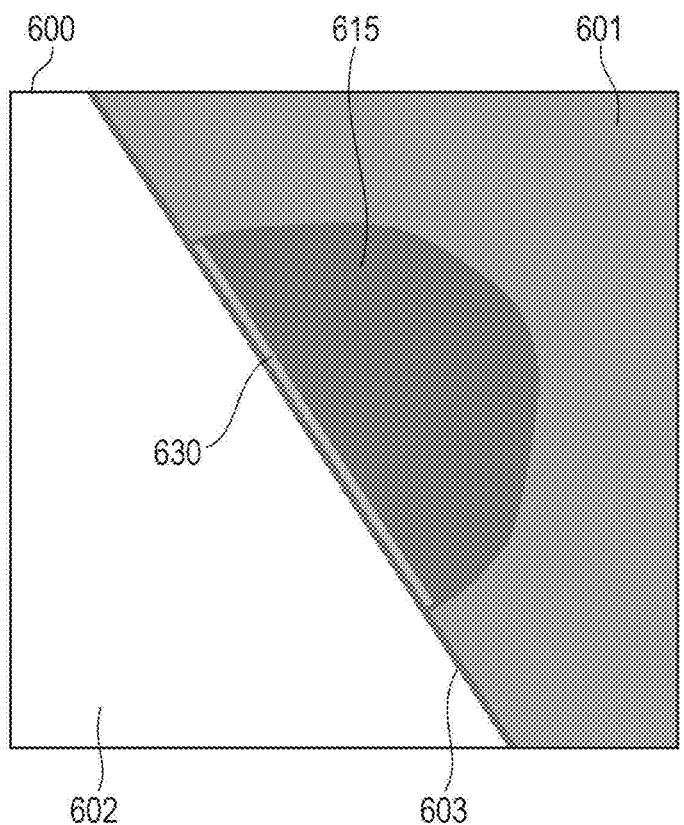
FIG. 6A illustrates a process performed by the image processing apparatus according to the embodiment of the present invention.
Figure 6B:
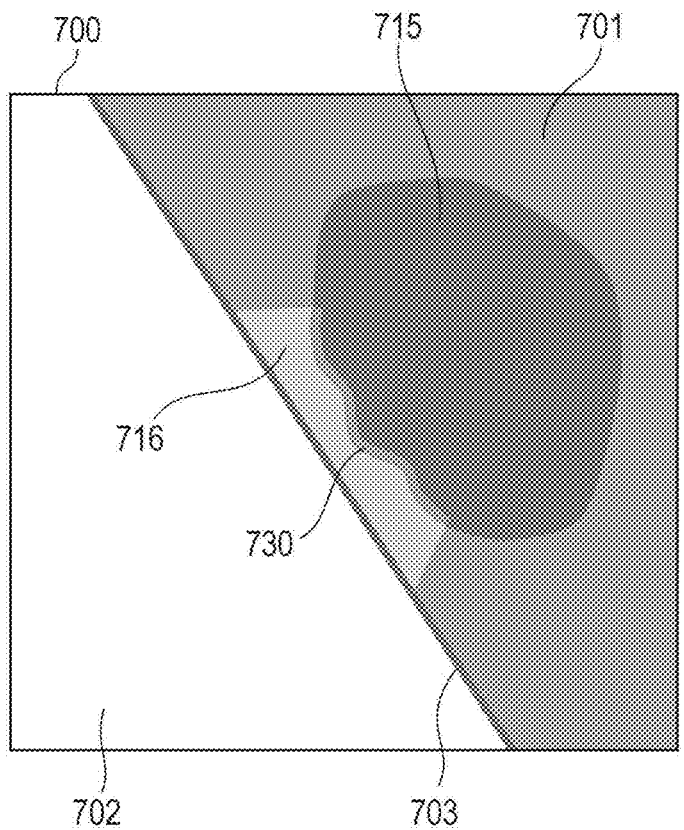
FIG. 6B illustrates a process performed by the image processing apparatus according to the embodiment of the present invention.

FIGS. 6A and 6B illustrate examples of the result of extracting the pleura and the pulmonary nodule in the two examples illustrated in FIGS. 5A and 5B, respectively. As a result of the process for extracting the pulmonary nodule 605 illustrated in FIG. 5A, an extracted pulmonary nodule 615 illustrated in FIG. 6A is obtained. A portion of the edge of the extracted pulmonary nodule 615 is attached to the pleural region 603 to create an attached region 630. The attached region 630 is a fourth region.

As a result of the process for extracting the pulmonary nodule 705 illustrated in FIG. 5B, an extracted pulmonary nodule 715 illustrated in FIG. 6B is obtained. In FIG. 6B, a non-extracted region 716 is found in a region including the pulmonary nodule 705 and the pleural indentation region 706. The non-extracted region 716 is not included in the extracted pulmonary nodule 715. This is because the pleural indentation region 706 takes a shape different from that of a typical pulmonary nodule or the pleural region 703. Since the technique described in step S1120 is based on information on the features of the shape of the target region, a region such as the pleural indentation region 706 may not be included in the extracted pulmonary nodule 715, as illustrated in FIG. 6B. A region included in the extracted pulmonary nodule 715 and attached to the pleural region 703, or an attached region 730 in the example illustrated in FIG. 6B, is a fourth region.

A doctor who observes the VOI image 600, the VOI image 700, and medical images including the VOI image 600 and the VOI image 700 may consider that an attached region where a pulmonary nodule, when observed, is attached to any other structure, or the fourth region, is not the true pulmonary nodule region, and thus may not take the attached region into account during observation. The following describes an example of identifying the fourth region to take into account during analysis a region that is likely to deform due to being located near any other structure.

In step S1130, the identification unit 1020 identifies a fourth region. Specifically, the identification unit 1020 identifies an attached region, which is a region where the pulmonary nodule region $V_{nodule}$ is located near the pleural region $V_{pleural}$, on the basis of the lung field region $V_{lung}$ and the pleural region $V_{pleural}$ extracted in step S1110 and the pulmonary nodule region $V_{nodule}$ extracted in step S1120.

First, the identification unit 1020 extracts a boundary region $S_{nodule}$ constituted by boundary pixels in the pulmonary nodule region $V_{nodule}$. Specifically, the identification unit 1020 determines, for each of the pixels belonging to the pulmonary nodule region $V_{nodule}$, whether any of the pixels (adjacent pixels) adjacent to the pixel "does not belong to the pulmonary nodule region $V_{nodule}$, but belongs to the lung field region $V_{lung}$". Then, if at least one adjacent pixel does not belong to the pulmonary nodule region $V_{nodule}$, but belongs to the lung field region $V_{lung}$, the at least one adjacent pixel is determined to be a pixel belonging to the boundary region $S_{nodule}$. In another example, the boundary region $S_{nodule}$ is extracted by, for example, performing a process using a differential filter or the like on the pulmonary nodule region $V_{nodule}$.

Figure 7:
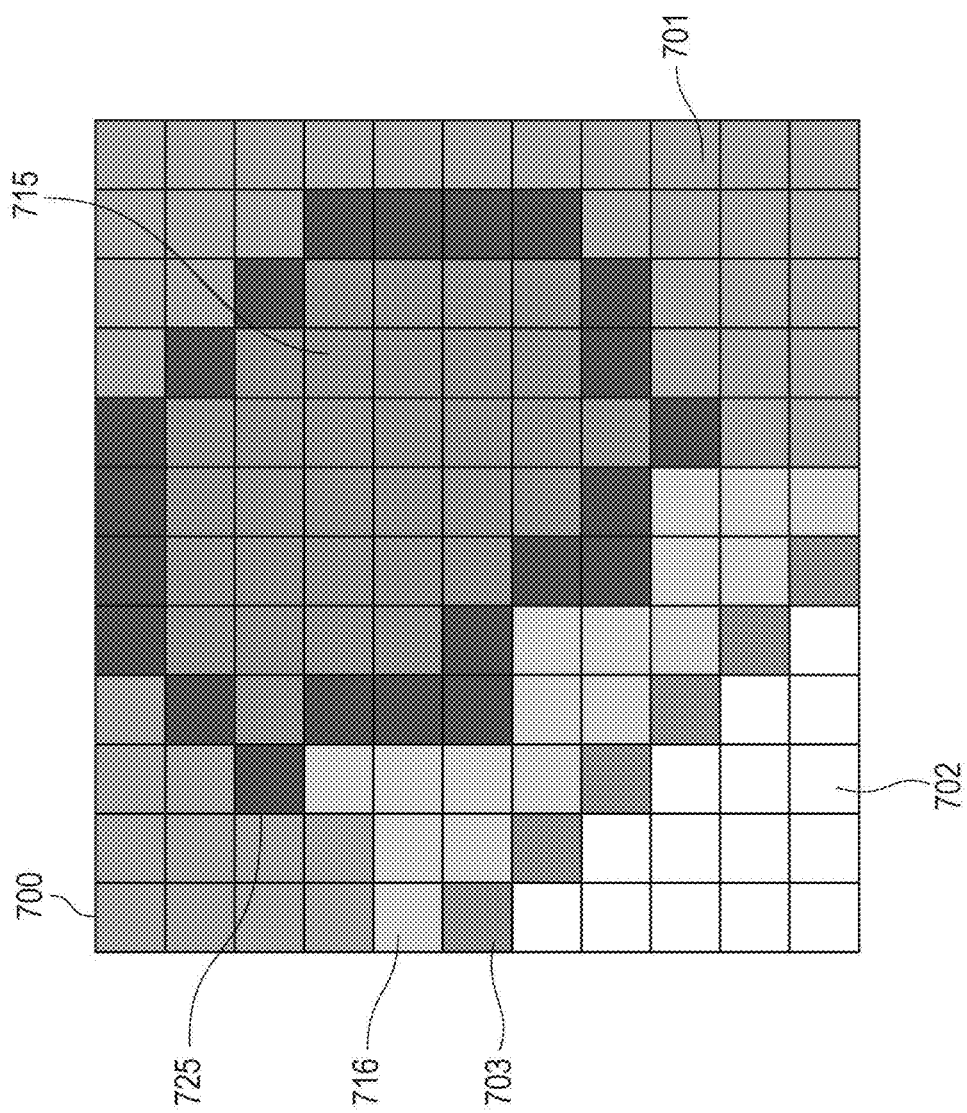
FIG. 7 illustrates a process performed by the image processing apparatus according to the embodiment of the present invention.

FIG. 7 illustrates an example process for acquiring pixels belonging to the attached region from the boundary region $S_{nodule}$. The identification unit 1020 acquires pixels belonging to the attached region on the basis of the distance from the acquired boundary region $S_{nodule}$ of the pulmonary nodule to the pleural region $V_{pleural}$. First, the identification unit 1020 searches for the shortest path from each of the pixels belonging to a boundary region 725 ($S_{nodule}$) to the pleural region 703 ($V_{pleural}$), and acquires the length of the shortest path (shortest path length).

The identification unit 1020 repeatedly performs a region growing process on each of the pixels belonging to the boundary region $S_{nodule}$. The identification unit 1020 repeatedly performs the region growing process until each pixel reaches the pleural region $V_{pleural}$, and acquires the number of repetitions of the region growing process as the shortest path length from the pixel to the pleural region $V_{pleural}$. That is, the identification unit 1020 acquires information concerning the distance between the second region and the first region on the basis of a process for searching for a pixel that is similar to a pixel in the boundary of the second region and a non-second region and that is not included in the second region or the first region. The region growing process is an example of the process described above, and the shortest path length is an example of the information concerning the distance. The following describes a process for acquiring a shortest path length in detail.

The identification unit 1020 sets the number of repetitions N of region growing of a specific pixel (hereinafter referred to as a pixel of interest) $P_{nodule-i}$ belonging to the boundary region $S_{nodule}$ to 0. The identification unit 1020 searches pixels within a neighboring region of the pixel of interest $P_{nodule-i}$ for a pixel satisfying region growing conditions as a growing pixel. That is, the pixel of interest $P_{nodule-i}$ is an example of a seed point of the region growing process. The number of repetitions N increases by 1 each time a search is performed. Then, the identification unit 1020 repeatedly performs the process described above on the found growing pixel until a termination condition is satisfied. The neighboring region described above refers to a region including pixels adjacent to the pixel of interest. In the region growing process, a neighboring region typically includes 4 or 8 pixels adjacent to the pixel of interest for a two-dimensional image. For a three-dimensional image, a neighboring region includes 6 or 26 pixels adjacent to the pixel of interest. The configuration of the neighboring region may be determined in accordance with the result of the region growing process.

The region growing conditions are (1) the growing pixel does not belong to the extracted pulmonary nodule 715, and (2) the density value falls within a predetermined range [$T_1$, $T_2$]. The values $T_1$ and $T_2$ are constants indicating the upper and lower limits of the density value that a pixel belonging to the non-extracted region may take, respectively. These values are determined from a medical image (learning image) similar to the input image. Specifically, first, the processing of steps S1110 and S1120 is actually applied to a plurality of learning images to acquire a non-extracted region that occurs between the first region and the second region. Then, the region growing process in step S1130 is performed. At this time, the region growing process is performed using a plurality of combinations of $T_1$ and $T_2$, and a combination of $T_1$ and $T_2$ is selected with which the most exact number of pixels belonging to the non-extracted region can be extracted by using the region growing process. The combination of $T_1$ and $T_2$ obtained in the way described above is used as the values $T_1$ and $T_2$ for the image processing apparatus 100. The values $T_1$ and $T_2$ may be set by the user.

The termination condition of the region growing process is that (1) a pixel belonging to the pleural region $V_{pleural}$ is present in the neighboring region of the pixel of interest $P_{nodule-i}$ or that (2) a pixel belonging to the pleural region $V_{pleural}$ is not present in the neighboring region of the pixel of interest $P_{nodule-i}$ nor is present a pixel satisfying the region growing conditions. When the termination condition (1) is satisfied, the identification unit 1020 finishes the region growing process and uses the number of repetitions N as the shortest path length of the pixel of interest. When the termination condition (2) is satisfied, the shortest path length is set to −1. Additionally, a termination condition that (3) the number of repetitions of region growing exceeds a preset value $T_{iteration}$ may be added as a parallel condition. When the termination condition (3) is satisfied, the value $T_{iteration}$ may be used as the shortest path length.

The identification unit 1020 performs the region growing process described above on each of the pixels belonging to the boundary region $S_{nodule}$, and acquires the shortest path length from the pixel to the pleural region $V_{pleural}$. In the example illustrated in FIG. 6A, the attached region 630 is in contact with the pleural region 603. The shortest path length is 0 according to the termination condition (1).

Figure 8:
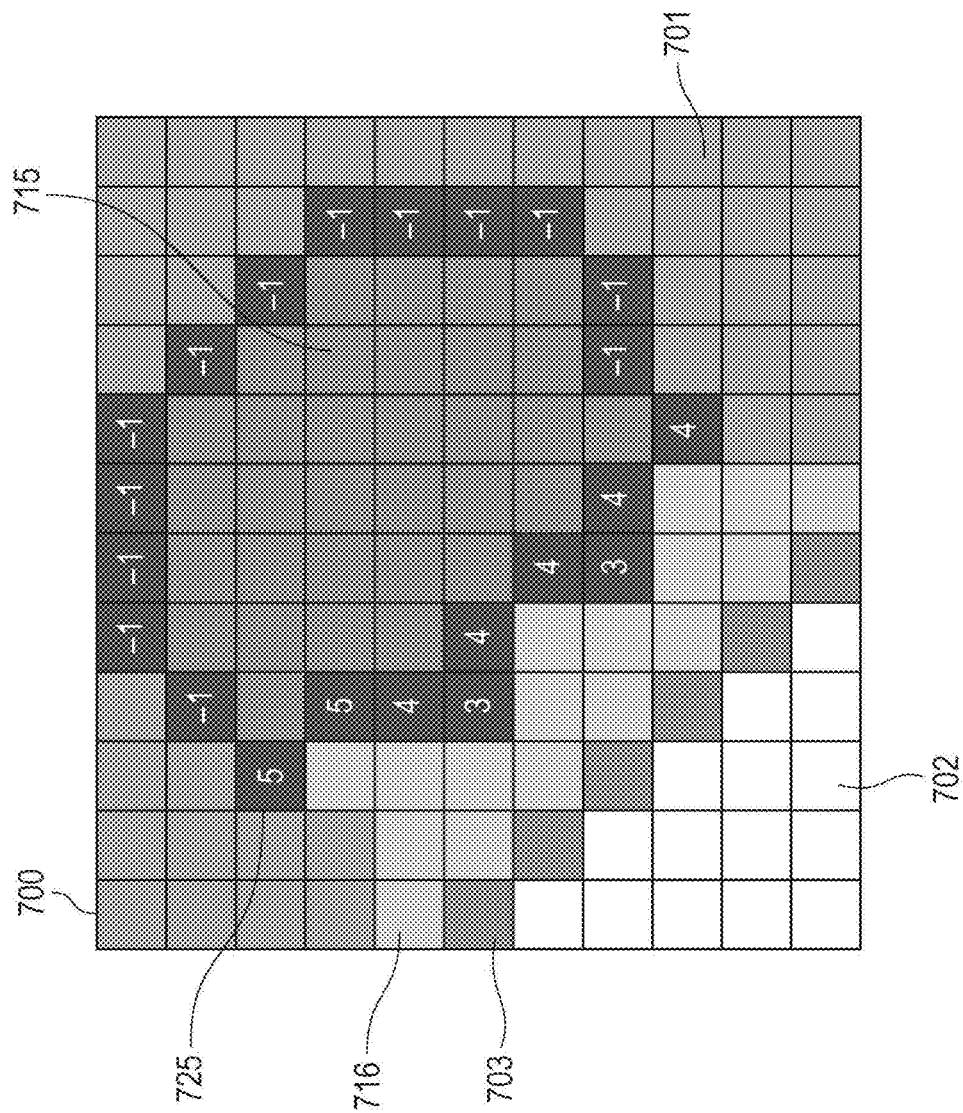
FIG. 8 illustrates a process performed by the image processing apparatus according to the embodiment of the present invention.

FIG. 8 illustrates an example of the result of the region growing process for the example illustrated in FIG. 7 (FIG. 6B). The identification unit 1020 repeatedly performs the region growing process until a pixel within the boundary region 725 reaches the pleural region 703 via the non-extracted region 716. As a result of the region growing process, for a pixel within the boundary region 725 that is in contact with the pleural region 703, the shortest path length is equal to the number of repetitions N of the region growing process according to the termination condition (1). For a pixel within the boundary region 725 that is not in contact with the pleural region 703 even though subjected to the region growing process, the shortest path length is −1 according to the termination condition (2).

The identification unit 1020 acquires an attached region $S_{attached}$ on the basis of the shortest path lengths for the respective pixels within the boundary region $S_{nodule}$. That is, the identification unit 1020 identifies a fourth region, which is included in the second region and is located near the first region, on the basis of the distance from the first region. The identification unit 1020 further acquires an unattached region on the basis of the shortest path lengths for the respective pixels within the boundary pixel $S_{nodule}$. That is, the identification unit 1020 identifies a third region different from the fourth region. In the first embodiment, the identification unit 1020 identifies a pixel having a shortest path length of −1 as an unattached region, that is, as a third region. The identification unit 1020 further identifies an attached region, that is, a fourth region, from among pixels each having a shortest path length of 0 or more.

The boundary region $S_{nodule}$ of the pulmonary nodule is sometimes in contact with, in addition to a pleural indentation region, a region having similar density values, such as a noise or blood vessel region. In this case, in the region growing process described above, a pixel within the boundary region $S_{nodule}$ is likely to reach the pleural region $V_{pleural}$ via a noise or blood vessel region. In general, the distance to the pleural region $V_{pleural}$ via a region such as blood vessels is longer than the distance to the pleural region $V_{pleural}$ via a pleural indentation region. Accordingly, for example, setting a threshold [0, $T_{attached}$] for the shortest path length of each of the pixels within the boundary region $S_{nodule}$ makes a pixel reaching the pleural region $V_{pleural}$ via a pleural indentation region and a pixel reaching the pleural region $V_{pleural}$ via any other region, such as blood vessels, distinguishable from each other. The value $T_{attached}$ may be set by the user or may be determined based on the learning image.

Figure 9:
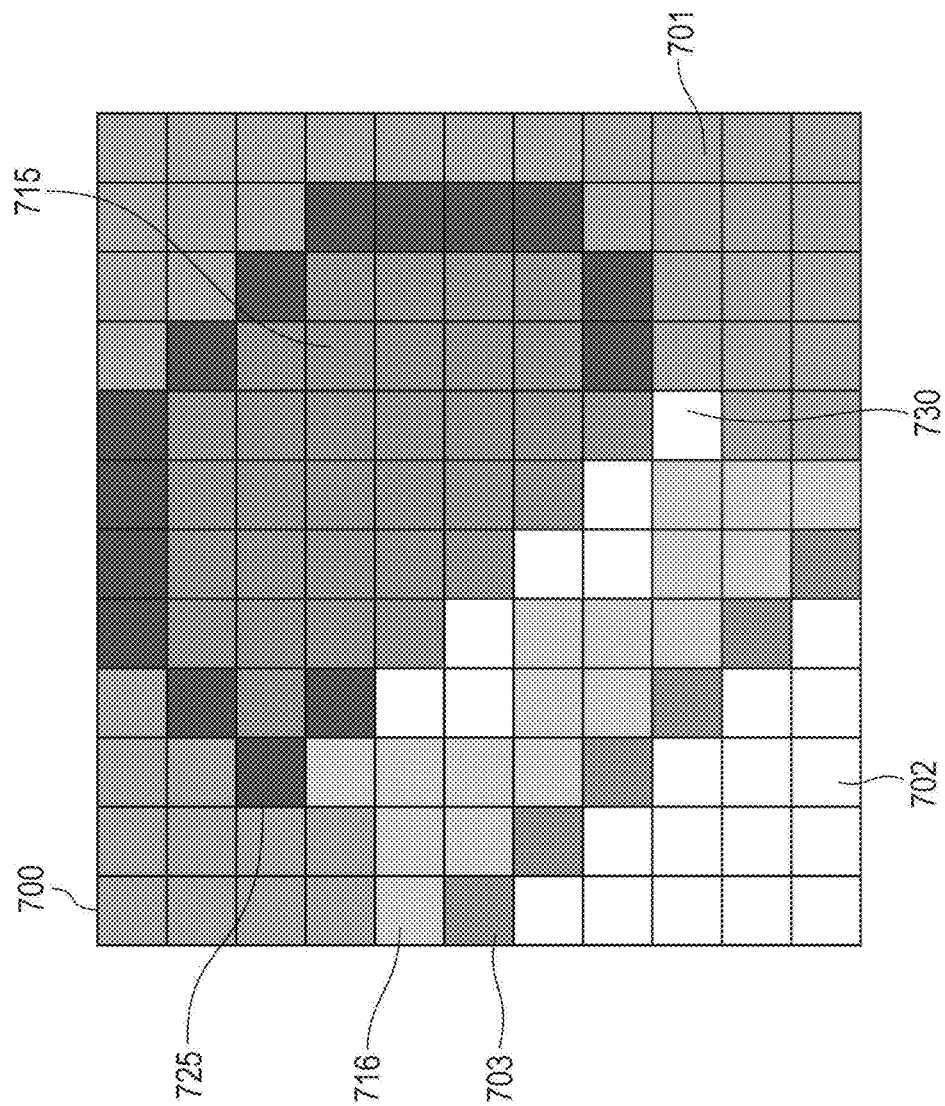
FIG. 9 illustrates a process performed by the image processing apparatus according to the embodiment of the present invention.

FIG. 9 illustrates an example of the attached region $S_{attached}$ (the attached region 730) identified by setting the threshold [0, 4] for the shortest path length of each pixel within the boundary region 725.

Depending on the accuracy of extraction of a pulmonary nodule region or the value of the threshold $T_{attached}$, the attached region $S_{attached}$ acquired using the threshold process described above may include a missing element region (a so-called hole). Further, the acquired attached region $S_{attached}$ may not be one concatenated region (single concatenated region), but may be divided into a plurality of regions. Accordingly, the identification unit 1020 may further perform a process for filling the hole generated in the attached region $S_{attached}$ or a process for integrating the plurality of separate attached regions $S_{attached}$ into a single concatenated region (hereinafter referred to as a connection process).

The connection process of the attached regions $S_{attached}$ is performed using, for example, a morphological operation. The identification unit 1020 dilates the attached regions $S_{attached}$ by using the morphological operation. Then, the identification unit 1020 acquires a region, which is obtained as a result of logical ANDs of the dilated attached regions obtained by morphological operation and the boundary region $S_{nodule}$, as a corrected attached region. The logical ANDs of the dilated attached regions and the boundary region $S_{nodule}$ are determined in order to limit an attached region obtained in the connection process within the boundary region $S_{nodule}$.

A hole generated in the attached region $S_{attached}$ can be filled by dilating the attached region $S_{attached}$ by morphological operation. A plurality of separate regions are dilated by morphological operation to bring each of the regions into contact with a neighboring region. Consequently, the plurality of regions can be integrated into a single concatenated region.

In step S1140, the feature value acquisition unit 1030 acquires a feature value, which is a value indicating a feature of the second region to be analyzed. Here, the acquisition of a feature value for the shape of a lesion (hereinafter referred to as a shape feature value), which is an example feature value, will be described, by way of example. Any type of feature value indicating a feature, other than a shape feature value, examples of which include a density value and the presence of a pleural indentation, may be acquired by the feature value acquisition unit 1030 in accordance with a known technique.

The feature value acquisition unit 1030 acquires a shape feature value of the pulmonary nodule region $V_{nodule}$ on the basis of the lung field region $V_{lung}$ and the pleural region $V_{pleural}$ extracted in step S1110, the pulmonary nodule region $V_{nodule}$ extracted in step 1120, and the attached region $S_{attached}$ acquired in step S1130.

The shape feature value may be a value indicating a feature, such as mean curvature of a boundary region of a pulmonary nodule, the proportion of a linear area, or the proportion of a convex area. For the purpose of using a feature value regarding a shape for CAD, it is desirable to accurately capture the shape of a lesion. However, the attached region $S_{attached}$ acquired in step S1130 may not correspond to the true boundary of the lesion region, and it is preferable to acquire the shape feature value taking the attached region $S_{attached}$ into account. In the first embodiment, the feature value acquisition unit 1030 acquires a shape feature value on the basis of the unattached region.

While an example has been described in which a morphological operation is performed prior to step S1140 in order to address the possible occurrence of a missing element region, this process is optional. For example, the identification unit 1020 may not perform a morphological operation, and the feature value acquisition unit 1030 may acquire feature values only for consecutive regions.

If the identification of an attached region fails in step S1130, the feature value acquisition unit 1030 acquires a shape feature value on the basis of the boundary region $S_{nodule}$. Alternatively, the feature value acquisition unit 1030 may also acquire a shape feature value on the basis of, for example, the boundary region $S_{nodule}$, without taking the attached region $S_{attached}$ into account.

In step S1150, the display control unit 1040 causes the display unit 160 to display a result of the processing up to step S1140. The display control unit 1040 causes the display unit 160 to display, as the result, a result of at least one process among the extraction of a pulmonary nodule region, the extraction of a pleural region, the identification of an attached region, and the acquisition of a feature value. The display control unit 1040 may display a feature value acquired without taking the attached region $S_{attached}$ into account and a feature value acquired on the basis of the unattached region in such a manner that these feature values can be compared with each other.

The display control unit 1040 may cause the display unit 160 to display information on the result described above and the input image in such a manner that the information is superimposed on the input image. The display control unit 1040 may generate information on a three-dimensional image on which the pieces of information described above are superimposed by using volume rendering, and cause the display unit 160 to display the three-dimensional image. Alternatively, the display control unit 1040 may generate a predetermined image of a cross section of the three-dimensional image with the superimposed information, and may cause the display unit 160 to display the image.

In the first embodiment, accordingly, even for a lesion region whose shape is not accurately extractable, such as an attached pulmonary nodule, a feature value for the shape can be acquired more accurately by taking the influence of the attachment of the lesion region to any other structure into account. The acquisition of an accurate feature value results in an improvement in the performance of CAD technology using the feature value, such as abnormal opacity region detection or assistance for benignity/malignancy judgment.

Modification of First Embodiment

A modification of a process for identifying the attached region $S_{attached}$ by using the identification unit 1020 in step S1130 will be described. The identification unit 1020 extracts at least a portion of the non-extracted region by using a threshold process, and combines the extracted region, the boundary region $S_{nodule}$, and the pleural region $V_{pleural}$ to generate a connected region. The identification unit 1020 identifies the attached region $S_{attached}$ on the basis of the distances between pixels within the connected region and the pleural region $V_{pleural}$.

Figure 10:
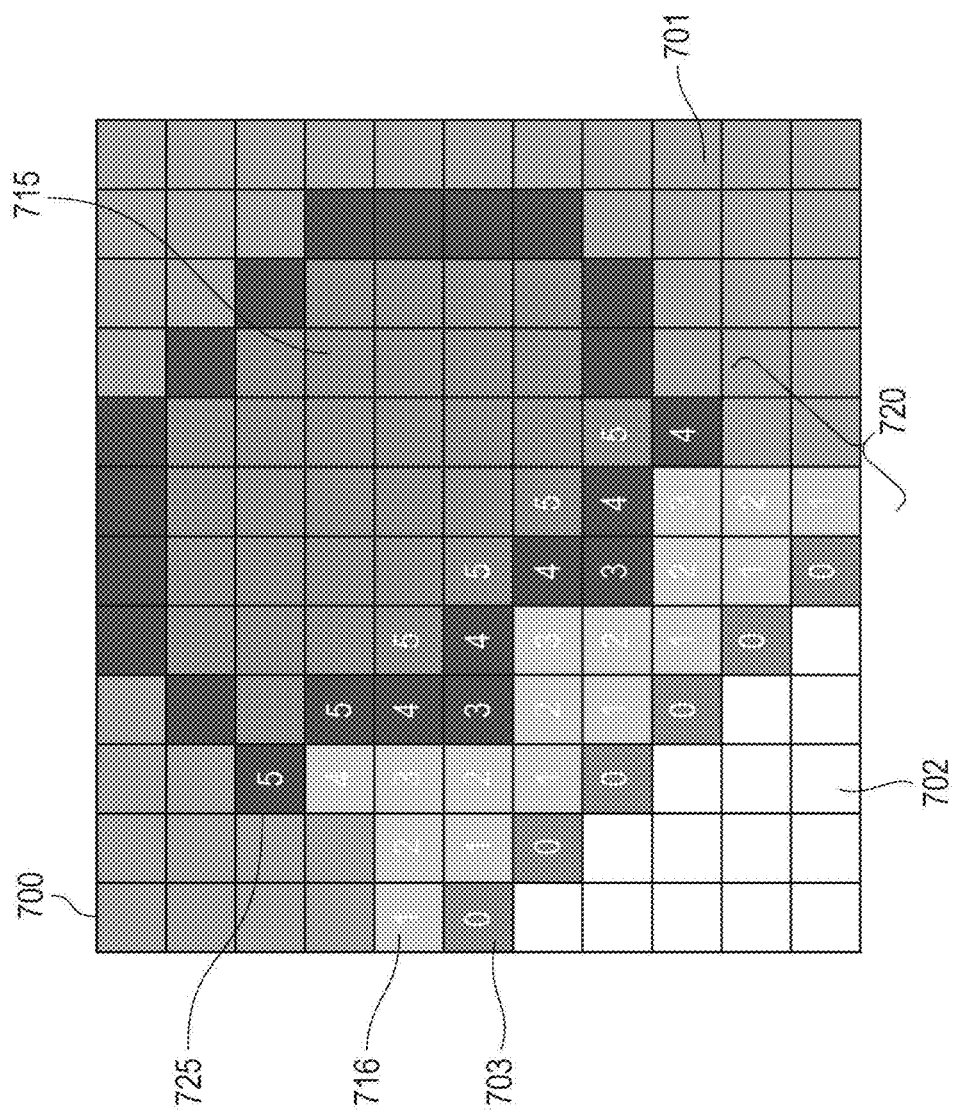
FIG. 10 illustrates a process performed by the image processing apparatus according to the embodiment of the present invention.

FIG. 10 illustrates an example process for acquiring the attached region $S_{attached}$ by using the connected region described above. The identification unit 1020 performs a threshold process on a portion of a lung field region 701, other than the extracted pulmonary nodule 715, and extracts a region having a higher density value than an air (alveolar) region as the non-extracted region 716. The identification unit 1020 acquires a region including three regions, namely, (1) the non-extracted region 716, (2) a region that is included in the pleural region 703 and that is in contract with the non-extracted region 716, and (3) a region that is included in the boundary region 725 of the extracted pulmonary nodule 715 and that is in contact with the non-extracted region 716, as a connected region 720. The identification unit 1020 acquires the distance between each of the pixels within the connected region 720 and the pleural region 703. The distance may be a Euclidean distance, a distance acquired by using the region growing method performed by the image processing apparatus 100 (a distance based on the number of repetitions of region growing), or a distance acquired using Dijkstra's algorithm or the A* search algorithm (a distance based on the length of an edge created between nodes). The identification unit 1020 identifies an attached region on the basis of the acquired distances for the respective pixels within the region (3) included in the connected region 720. Specifically, the identification unit 1020 identifies, for example, a pixel having a distance less than or equal to a threshold as an attached region.

Second Embodiment

As described above, lesions may occur near peripheral structures such as peripheral organs or other lesions. However, when a process of extracting a lesion region is performed, it is not necessarily determined whether the extracted lesion region is located near a peripheral structure from the extraction result. In a second embodiment, an example will be described of determining whether the first region and the second region are likely to be located near each other on the basis of the distance between the first region and the second region. Configurations, functions, or processes similar to those of the first embodiment are as described above and will not be described in detail.

Configuration of Image Processing Apparatus 200

An image processing apparatus 200 is, for example, a computer and has a hardware configuration similar to that in the example illustrated in FIG. 1.

Figure 11:
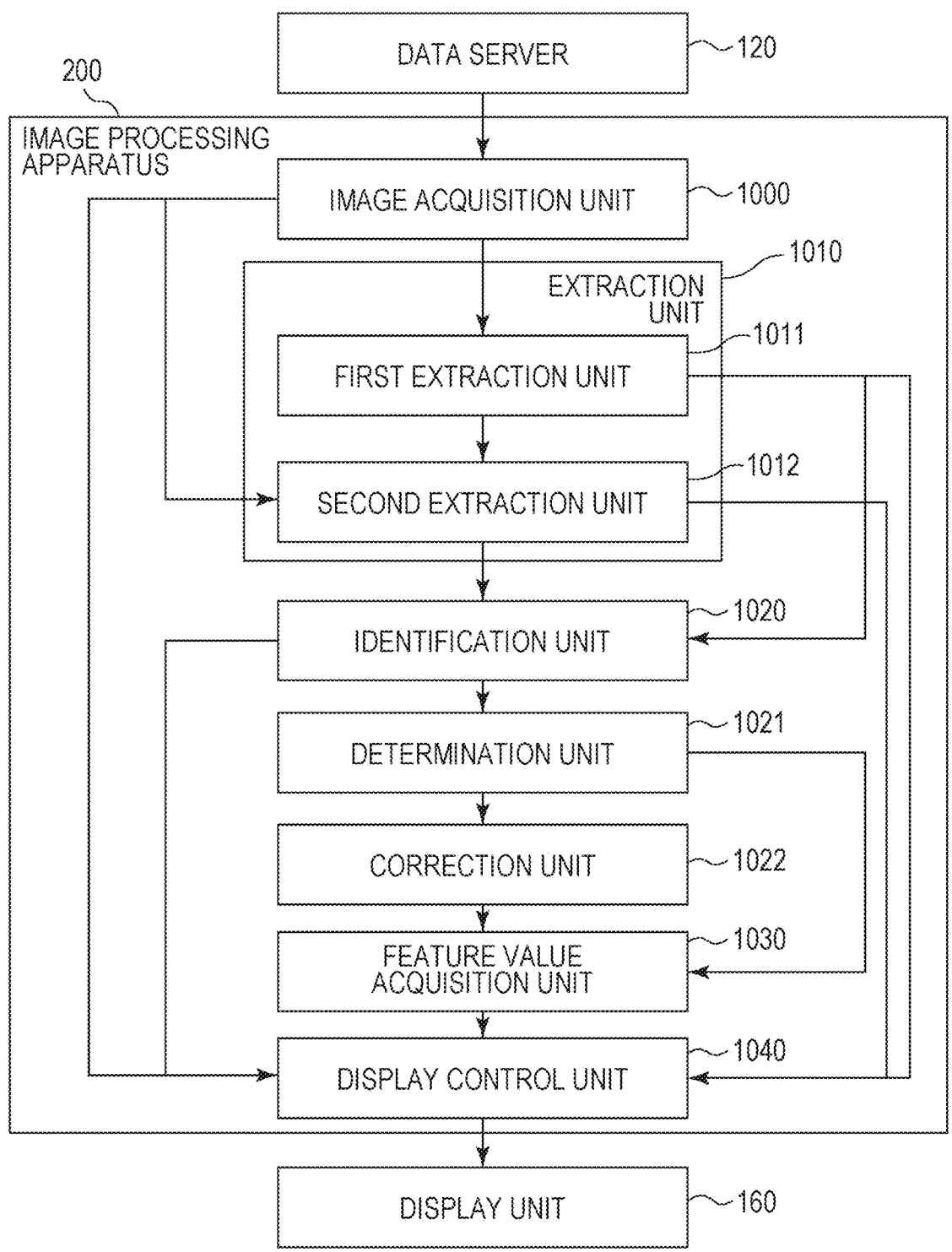
FIG. 11 illustrates an example functional configuration of an image processing apparatus according to a second embodiment.

FIG. 11 illustrates an example functional configuration of the image processing apparatus 200 according to the second embodiment. In the image processing apparatus 200, functional elements similar to those of the image processing apparatus 100 are assigned the same numerals as those in the example illustrated in FIG. 2. The image processing apparatus 200 includes the image acquisition unit 1000, the extraction unit 1010, the identification unit 1020, a determination unit 1021, a correction unit 1022, the feature value acquisition unit 1030, and the display control unit 1040. The extraction unit 1010 includes the first extraction unit 1011 and the second extraction unit 1012.

The determination unit 1021 determines whether, on the basis of information on an attached region identified by the identification unit 1020, a region of a structure to be analyzed, that is, the second region, is likely to be attached to any other structure. The determination unit 1021 further determines whether to correct the second region extracted by the second extraction unit 1012, on the basis of the information on the attached region. The determination unit 1021 is an example of determination means.

The correction unit 1022 corrects the second region extracted by the second extraction unit 1012. The correction unit 1022 is an example of correction means.

Regarding Series of Processes

FIG. 12 is a flowchart illustrating an example process performed by the image processing apparatus 200. In the following process, the processing operations are implemented by a processor such as the CPU 11 and are implemented by the processor executing a program stored in a memory such as the main memory 12, unless otherwise stated. Further, information processed by the processor is at least primarily stored in the memory.

The processing of steps S2100 to S2130 is similar to the processing of steps S1100 to S1130 according to the first embodiment described with reference to FIG. 3. In step S2130, on the basis of the distance between the second region, such as a pulmonary nodule region, and the first region, such as a pleural region, the fourth region, which is included in the second region and is likely to be located near the first region, and the third region, which is different from the fourth region, are identified.

In step S2132, the determination unit 1021 determines whether the second region is likely to be located near the first region on the basis of the identification of the fourth region in step S2130. Accordingly, it is determined that the extracted lesion region is likely to be located near a region of any other structure. In the second embodiment, the determination unit 1021 further determines whether to correct the extracted pulmonary nodule region in accordance with the identification of the fourth region. In the following, a process of correcting the extracted pulmonary nodule region is referred to as a correction process. The correction process is a process for, when the extracted pulmonary nodule region is smaller than the original pulmonary nodule region, making the size of the extracted pulmonary nodule region close to the original size.

Figure 13A:
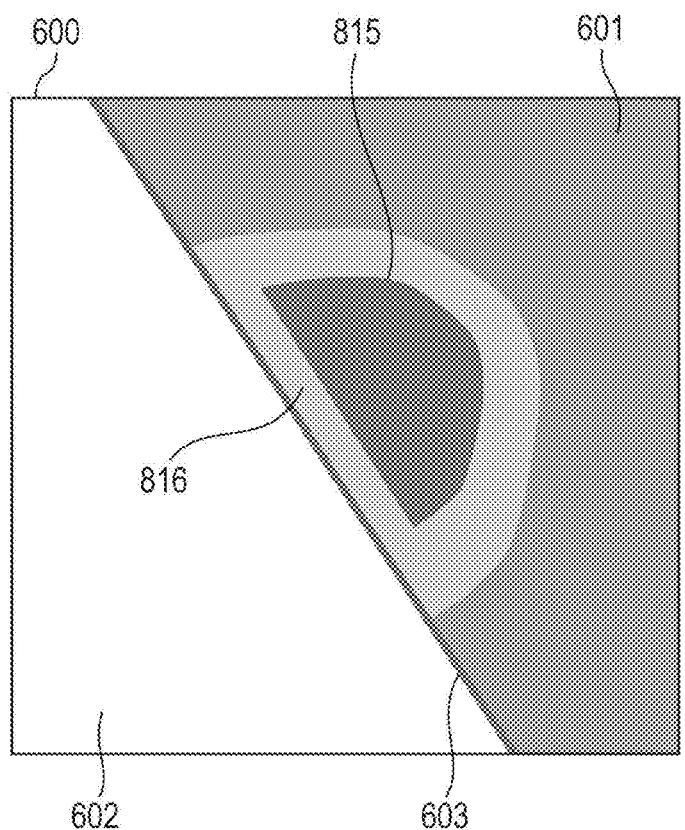
FIG. 13A illustrates a process performed by the image processing apparatus according to the embodiment of the present invention.
Figure 13B:
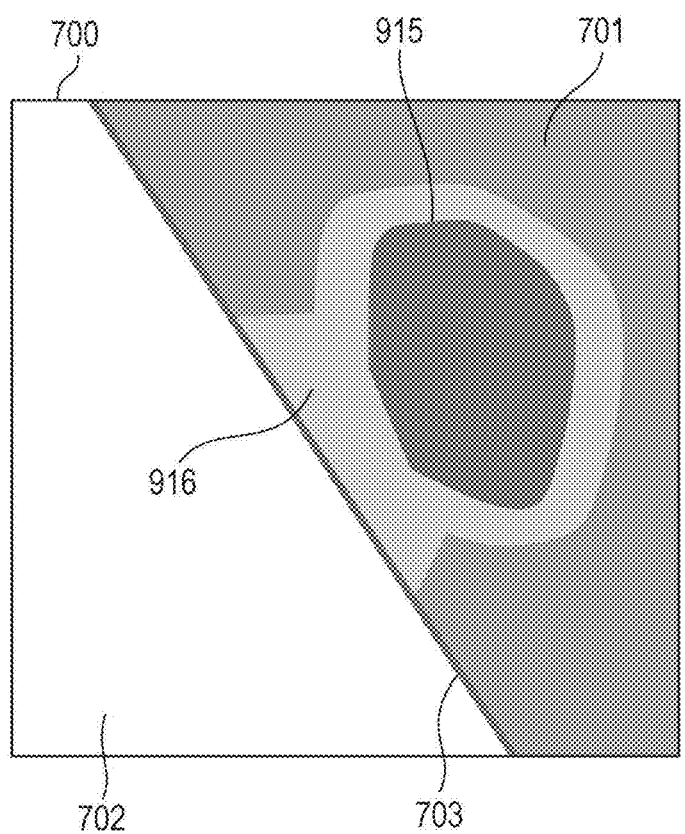
FIG. 13B illustrates a process performed by the image processing apparatus according to the embodiment of the present invention.
Figure 14:
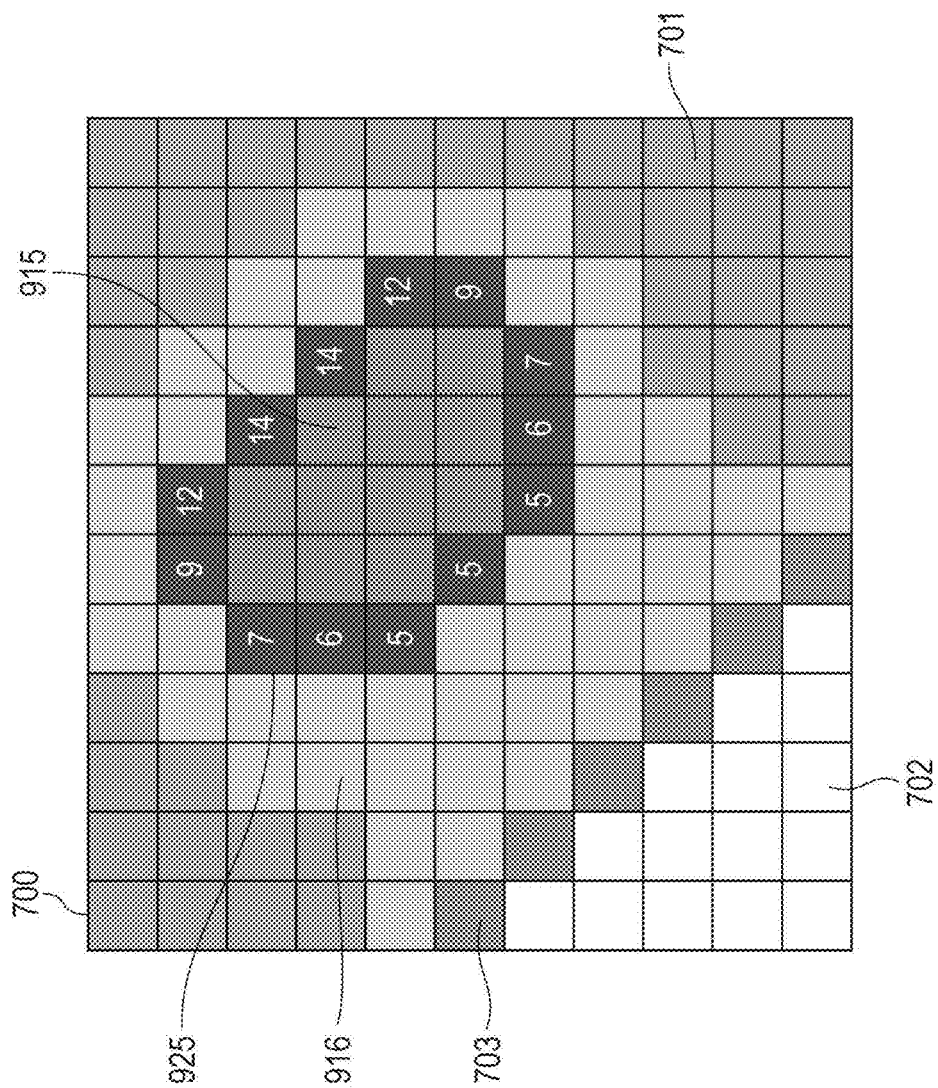
FIG. 14 illustrates a process performed by the image processing apparatus according to the embodiment of the present invention.

FIGS. 13A and 13B illustrate examples of a case where the pulmonary nodule region acquired in step S2120 is smaller than the original pulmonary nodule region. FIG. 14 illustrates an example of a result of performing the processing of step S2130 on the example illustrated in FIG. 13B.

In the example illustrated in FIG. 13B, the extraction of a portion of a region included in a pulmonary nodule fails, and a portion surrounding an extraction result 915 is a non-extracted region 916. In this case, as illustrated in FIG. 14, all the pixels included in a boundary region 925 are identified as being included in the attached region $S_{attached}$ through the processing of step S2130. It is not common that the entirety of the periphery of a pulmonary nodule is attached to any other structure. If the attached region $S_{attached}$ identified in step S2130 corresponds to all the pixels within the boundary region $S_{nodule}$, the determination unit 1021 determines that a correction process is necessary.

The determination unit 1021 acquires the number of pixels identified as being included in the attached region $S_{attached}$ among the pixels within the boundary region $S_{nodule}$ acquired in step S2120. A proportion $P_{surface}$, which is the ratio of the pixels identified as being included in the attached region $S_{attached}$ to the pixels within the boundary region $S_{nodule}$, is acquired. If the proportion $P_{surface}$ is greater than a predetermined threshold $T_{surface}$, the determination unit 1021 determines that the extraction result of the second region is not suitable and that a correction process needs to be performed. The threshold $T_{surface}$ may set by the user in advance or may be determined in accordance with machine learning. If it is determined that a correction process needs to be performed, the process proceeds to step S2135. If it is determined that a correction process is not necessary, the process proceeds to step S2140.

In step S2135, the correction unit 1022 corrects the extraction result of the second region acquired in step S2120. In the following, the pulmonary nodule region extracted in step S2120 is referred to as an old pulmonary nodule region.

Examples of the process for correcting the extraction result of the pulmonary nodule include a process of setting the old pulmonary nodule region as a foreground region (seed region) and growing the old pulmonary nodule region by using the level-set method, the graph-cut method, or the like. The correction unit 1022 may correct the old pulmonary nodule region by using a technique having features different from those of the region extraction technique used in step S2120. For example, in step S2120, when the second extraction unit 1012 extracts a second region by using a technique based on the total optimization for a region, such as the Graph-cut technique, then, in step S2135, the correction unit 1022 may utilize a region growing technique capable of representing local features. The region growing technique capable of representing local features is, for example, a technique for performing local optimization based on local features for density values, that is, the mean, variance, maximum, and minimum values of density values or density value profile in a neighboring region of the pixel of interest.

In accordance with the correction of the second region in step S2135, the size of the region determined to be a non-extracted region is reduced. The processing of step S2130 is performed again based on the extraction result of the second region obtained in step S2135 to identify an attached region.

The processing of step S2140 is similar to the processing of step S1140 described with reference to FIG. 3.

The processing of step S2150 is similar to the processing of step S1150 described with reference to FIG. 3. The display control unit 1040 may cause the display unit 160 to display information such as the pulmonary nodule regions, the attached regions, and the feature values, which are obtained before and after the correction in step S2135, in such a manner that these pieces of information can be compared with each other.

In the second embodiment, accordingly, a fourth region, which is a region where a region of a structure to be analyzed is located near any other structure, is identified to determine whether the structure to be analyzed is likely to be attached to any other structure. In the second embodiment, furthermore, it is possible to determine whether, on the basis of the result of identifying the fourth region, the region of the structure to be analyzed, that is, the result of extracting the second region, is suitable. If it is determined that the result of extracting the second region is not suitable, the result is corrected to more accurately extract the second region. Accordingly, the accuracy of a feature value for shape is enhanced, and the accuracy of CAD technology using the feature value is enhanced.

Other Embodiments

In the embodiments described above, a pulmonary nodule attached to the pleura on a chest CT image is to be processed. However, the type of modality for acquiring the target organ or lesion and an input image is not limited to that described above.

In the embodiments described above, the use of a partial image as illustrated in FIG. 5A or 5B has been described as an example of the input image input in step S1100. The partial image is, for example, an image that is centered on a specific region within a body region of a subject, such as a lesion. In the examples illustrated in FIGS. 5A and 5B, the first region and the second region are attached to each other or are located near each other with a pleural indentation region therebetween. The first region and the second region are separate, independent regions. The input image is not limited to that in the examples illustrated in FIGS. 5A and 5B, and may be, for example, an image showing a region of the entire lungs, as illustrated in FIG. 4. In the example illustrated in FIG. 4, the first region (pleural regions) surrounds the second region (pulmonary nodule regions). As in FIG. 4, even when the first region surrounds the second region, the embodiments described above are applicable. That is, a region that is included in the second region and that is located near (or attached to) the first region can be identified on the basis of the distance between the first region and the second region. The distance between the first region and the second region may be represented as, as in the embodiments described above, the number of times the region growing method is performed until a pixel within the second region reaches the first region. Alternatively, the distance may be represented as a geometric distance to the first region in the normal direction of the boundary of the second region. Alternatively, a portion of the first region may be extracted on the basis of the position of the second region, and a partial image including the extracted portion and the second region may be used as an input image, which is then subjected to the process described above. In any case, a region that is included in the second region and that is located near (or attached to) the first region can be identified.

In the embodiments described above, a region of the anatomical structure, such as the pleura, is used as a first region, and a region of a lesion, such as a pulmonary nodule, is used as a second region. However, the present invention is not limited to these embodiments. For example, both the first region and the second region may be regions of lesions, and an attached region can be identified by using a process similar to that described above.

The image processing apparatus 100 and the image processing apparatus 200 may further include a reasoning unit (not illustrated) for CAD. The reasoning unit (not illustrated) acquires a diagnostic name on the basis of a feature value acquired by the feature value acquisition unit 1030. The feature value acquisition unit 1030 may output a feature value to the reasoning unit (not illustrated) or may convert a feature value into another value corresponding to the feature value and then output the value to the reasoning unit. Another value corresponding to a feature value is, for example, information on a character string representing a state indicated by the feature value, or information on so-called findings.

The embodiments described above describe an example in which the shortest path length of an unattached region is set to −1 and the shortest path length of an attached region is set to 0 or the number of repetitions N of the region growing process. Accordingly, the identification unit 1020 can distinguish the unattached region and the attached region from each other by using the signs of the acquired shortest path lengths. The present invention is not limited to these embodiments, and any method capable of distinguishing the attached region and the unattached region from each other may be used.

The embodiments described above describe an example in which the identification unit 1020 acquires a shortest path length by using the region growing process. Path lengths obtained through the region growing process are typically geometric shortest path lengths, but are sometimes different from the lengths of geometric shortest paths. A shortest path length obtained through the region growing process is considered to satisfy the accuracy required in step S1130. To determine a more accurate shortest path length, a method based on the graph search algorithm may be used. The graph search algorithm is, for example, Dijkstra's algorithm or the A* search algorithm. In this case, the identification unit 1020 first performs a threshold process on the first region by using the threshold $[T_1, T_2]$ and then generates a graph whose nodes correspond to pixels within the obtained region. Then, the identification unit 1020 applies Dijkstra's algorithm or the A* search algorithm to each of the pixels belonging to the boundary region $S_{nodule}$ by using the pleural region $V_{pleural}$ as a search endpoint. In such a method, a shortest path is generated as a set of lines (edges) connecting nodes.

The embodiments described above describe an example in which an unattached region is identified on the basis of a shortest path length. However, the present invention is not limited to these embodiments. An unattached region may be acquired by, for example, identifying the attached region $S_{attached}$ and subtracting the identified attached region $S_{attached}$ from the boundary region $S_{nodule}$. Further, the fourth region and the third region may not have an exclusive relationship, and may partially overlap.

The embodiments described above describe an example in which the lesion to be analyzed is attached to any other structure. However, the present invention is not limited to these embodiments. For example, an image processing apparatus according to an embodiment of the present invention may extract a region of a lesion that is not attached to any other structure and use the region as the analytical target. Further, an image processing apparatus according to an embodiment of the present invention may be connected to, for example, a modality for acquiring a medical image such as a CT image. In this case, the image processing apparatus may be a control device for controlling the modality.

The present invention can also be implemented using a process for providing a program that implements one or more functions in the embodiments described above to a system or device via a network or a storage medium and for reading and executing the program by one or more processors in a computer of the system or device. The present invention can also be implemented by a circuit (e.g., an ASIC) that implements one or more functions.

An image processing apparatus in each of the embodiments described above may be implemented as a standalone device or may be implemented as an arrangement where a plurality of devices are combined so as to be capable of communicating with each other to execute the processes described above, and both implementations are included in an embodiment of the present invention. The processes described above may be executed by a shared server device or a server group. An image processing apparatus and a plurality of devices making up an image processing system are desirably capable of performing communication at a predetermined communication rate, and do not need to be located in the same facility or even in the same country.

Embodiments of the present invention include an embodiment in which a software program that implements the functions of the embodiments described above is provided to a system or device and a computer of the system or device reads and executes code of the provided program.

Accordingly, the program code that is installed in a computer to allow the computer to implement processes according to the embodiments is in itself an embodiment of the present invention. Further, in accordance with instructions included in the program read by the computer, an OS or the like operating on the computer may perform some or all of the actual processes, and such processes may also implement the functions of the embodiments described above.

The embodiments described above may also be combined as appropriate, and such a combination is also included in an embodiment of the present invention.

The present invention is not restricted to the embodiments described above, and various changes and modifications can be made without departing from the spirit and scope of the present invention. Accordingly, the following claims are appended to make public the scope of the present invention.

In an image processing apparatus according to an embodiment of the present invention, a feature value is acquired using a region that is included in a region to be analyzed and that is identified on the basis of the distance from any other region. Accordingly, the region can be analyzed taking into account that the region is located near any other region.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
one or more computer-readable storage media storing instructions; and
one or more processors in communication with the one or more computer-readable media, wherein the one or more computer-readable storage media and the one or more processors cooperate to cause the image processing apparatus to perform operations including:
extracting a first region and a second region inside the first region and different from the first region from a medical image;
identifying a third region, the third region being included in the second region and being at a distance greater than or equal to a threshold from the first region, wherein the identifying acquires information concerning the distance through a process for searching for a pixel, the pixel being similar to a pixel within a boundary of the second region with a region other than the second region and not being included in the second region or the first region; and
acquiring a feature value on the basis of the third region, the feature value being a value indicating a feature of the second region.

2. The image processing apparatus according to claim 1, wherein the identifying acquires information concerning the distance on the basis of the number of repetitions of a region growing process performed under a predetermined condition using a pixel within a boundary with a region other than the second region as a seed point.

3. The image processing apparatus according to claim 1, wherein the operations further include:
correcting the second region extracted by the extracting on the basis of information on a fourth region identified by the identifying.

4. An image processing apparatus comprising:

one or more computer-readable storage media storing instructions; and one or more processors in communication with the one or more computer-readable media, wherein the one or more computer-readable storage media and the one or more processors cooperate to cause the image processing apparatus to perform operations including:

extracting a pleural region and a nodule area from a medical image;

identifying an attached region on the basis of the pleural region, the attached region being included in the nodule area and being likely to be attached to the pleural region, thereby identifying an area as a sub-region, the area being included in the nodule area and not including the attached region, wherein an area located at a distance less than or equal to a threshold from the pleural region is identified as the attached region; and acquiring a feature value on the basis of the sub-region, the feature value being a value indicating a feature of the nodule area.

5. The image processing apparatus according to claim 4, wherein the operations further include:

correcting the nodule area extracted by the extracting on the basis of information on the attached region identified by the identifying.

6. An image processing method comprising:

extracting a pleural region and a nodule area from a medical image;

identifying an attached region on the basis of the pleural region, the attached region being included in the nodule area and being likely to be attached to the pleural region, thereby identifying an area as a sub-region, the area being included in the nodule area and not including the attached region, wherein an area located at a distance less than or equal to a threshold from the pleural region is identified as the attached region; and acquiring a feature value on the basis of the sub-region, the feature value being a value indicating a feature of the nodule area.

* * * * *